(12) United States Patent
Ries et al.

(10) Patent No.: US 8,906,105 B2
(45) Date of Patent: Dec. 9, 2014

(54) SYSTEMS AND METHODS FOR MOBILE BEARING PROSTHETIC KNEE

(75) Inventors: Michael D. Ries, Tiburon, CA (US);
Mark Mooradian, Phoenix, AZ (US);
Daniel F. Jusitn, Logan, UT (US);
Joshua A Butters, Chandler, AZ (US)

(73) Assignee: Michael D. Ries, Tiburon, CA (US)

( * ) Notice: Subject to any disclaimer, the term of this patent is extended or adjusted under 35 U.S.C. 154(b) by 769 days.

(21) Appl. No.: 12/606,326

(22) Filed: Oct. 27, 2009

(65) Prior Publication Data

US 2011/0040387 A1    Feb. 17, 2011

Related U.S. Application Data

(60) Provisional application No. 61/233,081, filed on Aug. 11, 2009.

(51) Int. Cl.
*A61F 2/38* (2006.01)
*A61F 2/30* (2006.01)

(52) U.S. Cl.
CPC .............. *A61F 2/3868* (2013.01); *A61F 2/385* (2013.01); *A61F 2/3886* (2013.01); *A61F 2002/30616* (2013.01); *A61F 2002/30878* (2013.01); *A61F 2002/30884* (2013.01)
USPC .................................... 623/20.27; 623/20.29

(58) Field of Classification Search
USPC ................. 623/20.15, 20.27, 20.29
See application file for complete search history.

(56) References Cited

U.S. PATENT DOCUMENTS

| | | | |
|---|---|---|---|
| 5,071,438 A * | 12/1991 | Jones et al. ............... | 623/20.29 |
| 5,330,533 A | 7/1994 | Walker | |
| 5,330,534 A | 7/1994 | Herrington | |
| 5,387,240 A | 2/1995 | Pottenger | |
| 5,413,604 A * | 5/1995 | Hodge ...................... | 623/20.28 |
| 5,480,446 A | 1/1996 | Goodfellow | |

(Continued)

FOREIGN PATENT DOCUMENTS

| | | |
|---|---|---|
| DE | 202010000037 | 3/2010 |
| WO | WO0182842 A1 | 11/2001 |
| WO | WO2006118822 | 11/2006 |
| WO | WO2011059759 | 5/2011 |

OTHER PUBLICATIONS

Biomet *AGC Total Knee System* Product Brochure May 2009.

(Continued)

*Primary Examiner* — Bruce E Snow
*Assistant Examiner* — Melissa Hoban
(74) *Attorney, Agent, or Firm* — Snell & Wilmer L.L.P.

(57) ABSTRACT

A knee prosthesis including a femoral implant, a tibial implant, a tibial insert and a cam post. The femoral implant is secured to a femur and has a cam feature and condyles. The tibial implant is secured to a tibia. The tibial insert comprises a medial cavity with a rotational axis. The tibial insert has articulating surfaces that match the contours of the condyles of the femoral implant. The tibial insert has a medial boss that aligns with the medial cavity allowing it to rotate about the rotational axis. A cam post is secured to the tibial implant and passes through a channel of the tibial insert providing anterior and posterior stops for the rotation of the tibial insert about the rotational axis. The cam post interacts with the femoral implant cam feature and, with the tibial insert, allows more anatomically correct rollback and femoral external rotation during knee flexion.

12 Claims, 32 Drawing Sheets

(56) References Cited

U.S. PATENT DOCUMENTS

| | | | |
|---|---|---|---|
| 5,658,342 A | 8/1997 | Draganich | |
| 5,755,801 A | 5/1998 | Walker | |
| 5,879,392 A | 3/1999 | McMinn | |
| 5,879,394 A | 3/1999 | Ashby | |
| 5,928,286 A | 7/1999 | Ashby | |
| 6,013,103 A | 1/2000 | Kaufman | |
| 6,039,764 A | 3/2000 | Pottenger | |
| 6,080,195 A | 6/2000 | Colleran | |
| 6,099,570 A * | 8/2000 | Livet et al. | 623/20.21 |
| 6,165,223 A * | 12/2000 | Metzger et al. | 623/20.27 |
| 6,203,576 B1 | 3/2001 | Afriat | |
| 6,214,052 B1 | 4/2001 | Burkinshaw | |
| 6,296,666 B1 | 10/2001 | Gardner | |
| 6,413,279 B1 | 7/2002 | Metzger | |
| 6,558,427 B2 | 5/2003 | Leclercq | |
| 6,629,999 B1 | 10/2003 | Serafin | |
| 6,764,516 B2 | 7/2004 | Pappas | |
| 6,797,005 B2 | 9/2004 | Pappas | |
| 6,972,039 B2 | 12/2005 | Metzger | |
| 6,974,481 B1 | 12/2005 | Carson | |
| 6,986,791 B1 | 1/2006 | Metzger | |
| 7,105,027 B2 | 9/2006 | Lipman | |
| 7,232,465 B2 | 6/2007 | Keller | |
| 7,572,292 B2 | 8/2009 | Crabtree | |
| 7,658,767 B2 | 2/2010 | Wyss | |
| 2001/0003803 A1 | 6/2001 | Leclercq | |
| 2003/0153980 A1 | 8/2003 | Brack | |
| 2005/0209702 A1 | 9/2005 | Todd | |
| 2007/0100462 A1 | 5/2007 | Lang | |
| 2007/0100463 A1 | 5/2007 | Aram | |
| 2007/0135925 A1 | 6/2007 | Walker | |
| 2007/0135926 A1 | 6/2007 | Walker | |
| 2008/0009950 A1 | 1/2008 | Richardson | |
| 2008/0021566 A1 | 1/2008 | Peters | |
| 2008/0097616 A1 * | 4/2008 | Meyers et al. | 623/20.29 |
| 2008/0114464 A1 | 5/2008 | Barnett | |
| 2008/0119940 A1 | 5/2008 | Otto | |
| 2008/0243259 A1 | 10/2008 | Lee | |
| 2008/0300690 A1 | 12/2008 | Burstein | |
| 2009/0043396 A1 | 2/2009 | Komistek | |
| 2009/0088861 A1 | 4/2009 | Tuke | |
| 2009/0149964 A1 | 6/2009 | May | |

OTHER PUBLICATIONS

Biomet *Alpina APR* Product Info Website: http://www.biomet.co.uk/index.php?id=17313 Jan. 3, 2007.

Biomet Europe, *Vanguard System Summary* May 2009.

Corin *Corin Rotaglide & Mobile Bearing*, Product Brochure, Jan. 20, 2011 p. 1-3.

Depuy *Finsbury Dual Bearing Knee*, Feb. 10, 2010.

Depuy *LCS Complete Product Brochure*, May 2009.

Depuy *Sigma Rotating Platform* Product Brochure, May 2009.

Kyocera *Kyocera Bisurface Mechanical Comparison of 2 Posterior Stabilizing Designs*, Journal of Arth. col. 17 No. 5 2002.

Medacta *GMK Primary* Product Brochure Nov. 26, 1999 Rev. 00[1].

Smith & Nephew *Journey BCS* Product Brochure May 2009.

Spherocentric Knee *Biomechanical Testing and Clinical Trial*, JBJS 1977 Vo. 59 pp. 602-616.

Stryker *NRG Product Brochure*, Aug. 2009.

Wright Medical *MK056-206 Advance*, Family Brochure May 2009.

Zimmer *NexGen Implant Options*, Product Brochure Aug. 2009.

Zimmer *NexGen Mobile Bearing LPS Flex and LPS Mobile Bearing Knee*, Product Brochure Aug. 2009.

Smith & Nephew *Journey BCS ORS White Paper Poster #1987 at 2008 ORS Annual Meeting* San Francisco, CA.

Smith & Nephew Journey BCS *Design Rationale* 2006.

Banks, Scott PhD; *Knee Motions During Maximum Flexion in Fixed and Mobile-Bearing Arthroplasties*, Clinical Orthopaedics and Related Research No. 410, pp. 131-138 2003.

Walker, Peter S.; Biomechanical Principles of Total Knee Replacement Design, Basic Orthopaedic Biomechanics 2nd ed. 1997 pp. 461-493.

Douglas, Dennis A.; *Factors Affecting Flexion after Total Knee Arthroplasty*, Clinical Orthopaedics and Related Research No. 464, pp. 53-60 2007.

Kelly, Michael A. *In vivo kinematic evaluation and design considerations related to high flexion in total knee arthroplasty.* Journal of Biomechanics 38 (2005) 277-284.

Halloran, Jason P.; *Eplicit finite element modeling of total knee replacement mechanics*, Journal of Biomechanics 38 (2005) 323-331.

Morra, Edward A.; *Polymer Insert Stress in Total Knee Designs During High Flexion Activites: A Finite Element Study*, Orthopaedic Research Laboratories Cleveland Ohio AAOS 2005 pp. 1-4.

Greenwald, Seth A. *Mobile-Bearing Knee Systems: Ultra-High Molecular Weght Polyethylene Wear and Design Issues*, AAOS Instructional Course Lectures, vol. 54 2005 pp. 195-205.

Vertullo, Christopher J. *Mobile Bearings in Primary Knee Arthroplasty* Journal of the American Academy Orthopaedic Surgeons vol. 9, No. 6 Nov./Dec. 2001.

Morra, Edward A.; *The Influence of Contemporary Knee Design on High Flexion II: A Kinematic Coparison with the Normal Knee.* Orthopaedic Research Laboratories Cleveland, Ohio, AAOS 2009.

Zimmer: Comprehensive Natureal-Knee Family. (2006) Website: www.Zimmer.co.uk/z/ctl/op/global/action/1/is/7802/template/MP.com Zimmer: Gender Solutions Natural-Knee Flex System. Product Brochure (2007).

Cosset; Larry MD.: *Evolution of the Low Contact Stress (LCS) Complete Knee System.* Ortrhopedics, Feature Article: Sep. 2006 vol. 29, No. 9 Supplement pp. S17-S22.

Office Action dated Aug. 25, 2014 in U.S. Appl. No. 12/914,799.

\* cited by examiner

SYSTEMS AND METHODS FOR MOBILE BEARING PROSTHETIC KNEE

CROSS-REFERENCE TO RELATED APPLICATIONS

This application claims the benefit of the following, which is incorporated herein by reference:

Pending prior U.S. Provisional Patent Application No. 61/233,081 filed 11 Aug. 2009, which carries Applicants' docket no. MDR-4 PROV, and is entitled MOBILE BEARING PROSTHETIC KNEE.

BACKGROUND OF THE INVENTION

1. The Field of the Invention

The present invention relates generally to a total knee replacement by using a mobile bearing prosthetic knee, and more particularly, providing a more functionally correct motion of the prosthetic knee similar to kinematic motion of a normal, non-prosthetic knee, during knee flexion.

2. The Relevant Technology

One attribute of normal knee flexion is that, as the knee flexes, the contact points of the femur on the tibia move posteriorly. This posterior movement of the contact points is known as rollback. Also, normal knee rollback is much more pronounced on the lateral side of the knee than the medial side, which results in femoral external rotation during knee flexion.

Other prosthetic knees currently on the market do not use two separate fully guided motion paths, and as a consequence may not reproduce normal knee kinematics and need to use wear components made of polyethylene, or similar material, to accommodate the less-guided sliding that occurs during knee flexion. These existing methods and procedures may not be as effective as desired. There is a need to have a tibial insert of a prosthetic knee roll back on a medial pivot axis causing greater rollback on the lateral side than the medial side, like a normal, non-prosthetic knee.

BRIEF DESCRIPTION OF THE DRAWINGS

Various embodiments of the present invention will now be discussed with reference to the appended drawings. It is appreciated that these drawings depict only typical embodiments of the invention and are therefore not to be considered limiting of its scope.

DETAILED DESCRIPTION OF THE PREFERRED EMBODIMENTS

The present invention relates to systems and methods used in orthopedic surgery, and in particular, to total knee arthroplasty. Those of skill in the art will recognize that the systems and methods described herein may be readily adapted for any total joint arthroplasty procedure. Those of skill in the art will also recognize that the following description is merely illustrative of the principles of the invention, which may be applied in various ways to provide many different alternative embodiments. This description is made for the purpose of illustrating the general principles of this invention and is not meant to limit the inventive concepts in the appended claims.

Figure 1:
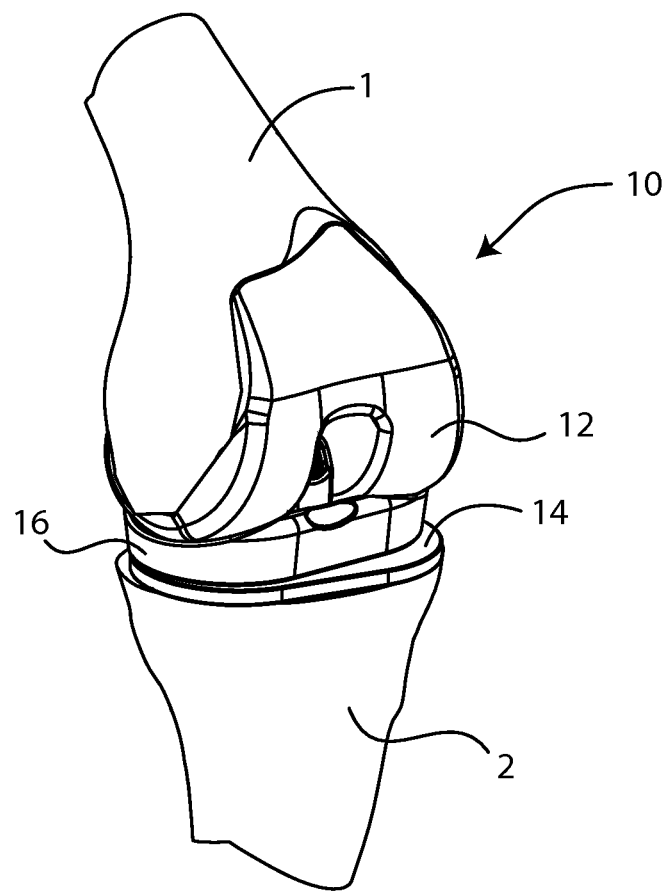
FIG. 1 illustrates a perspective view of the prosthesis, with a femur, a tibia, a tibial baseplate, a tibial insert, a femoral implant and a reference arrow diagram.
Figure 1:
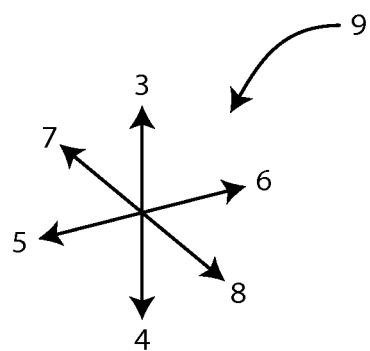

Referring to FIG. 1, a perspective view illustrates a mobile bearing knee prosthesis 10 according to one embodiment of the invention, implanted in a knee. This figure and subsequent figures may be oriented according to the reference arrow diagram 9, having a superior direction 3, an inferior direction 4, a medial direction 5, a lateral direction 6, a posterior direction 7, and an anterior direction 8. In this application, "left" and "right" are used with reference to a posterior view. "Medial" refers to a position or orientation toward a sagittal plane (i.e., plane of symmetry that separates left and right sides of the body from each other), and "lateral" refers to a position or orientation relatively further from the sagittal plane. The knee prosthesis 10 may comprise a tibial baseplate 14, a tibial insert 16 and femoral implant 12.

Figure 2:
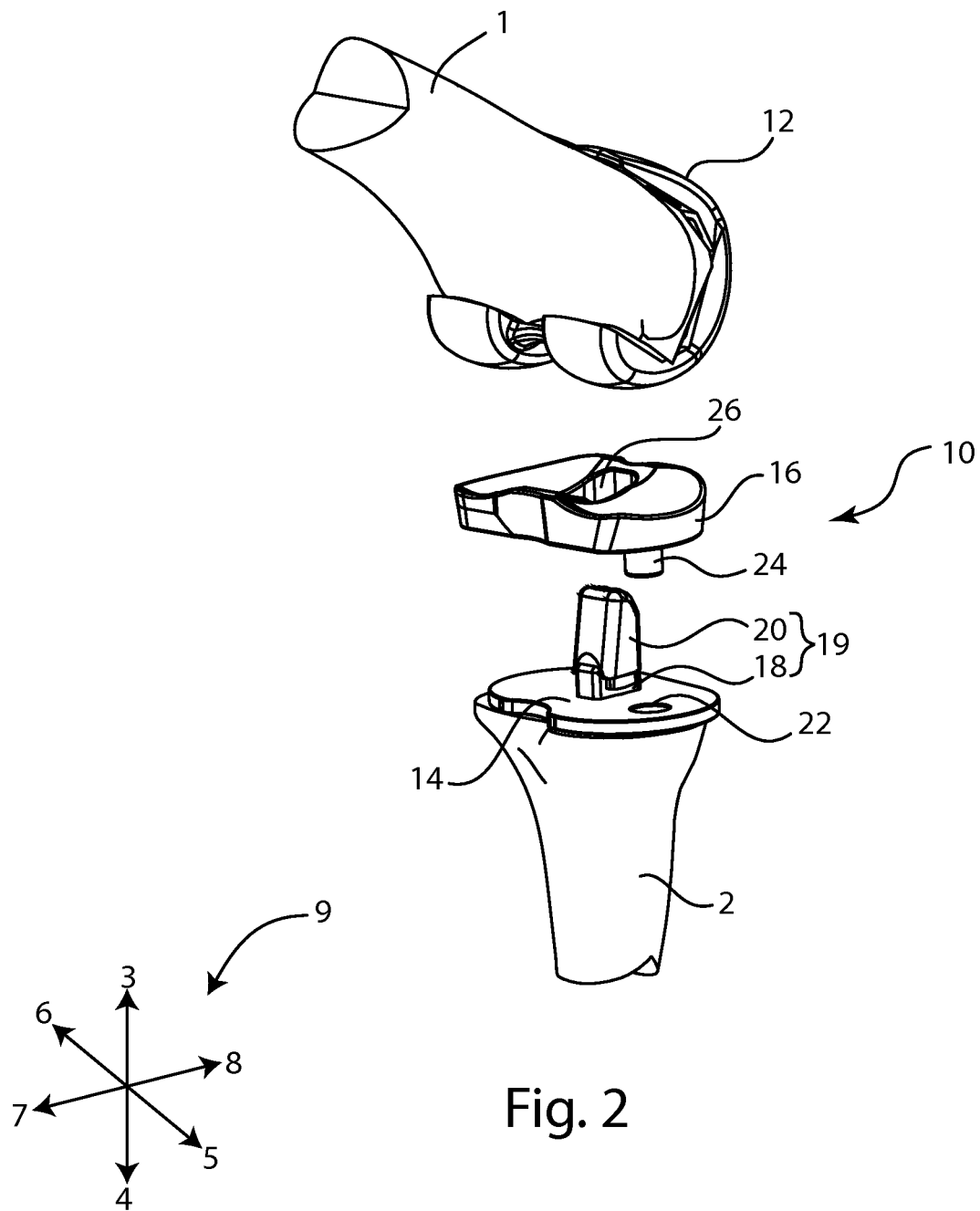
FIG. 2 illustrates an exploded perspective view of the prosthesis of FIG. 1 with the femur, the tibia, the tibial baseplate with a tibial baseplate aperture, the tibial insert with a tibial insert boss and a tibial insert hole, the femoral implant, and a cam post with an outer sleeve.
Figure 3:
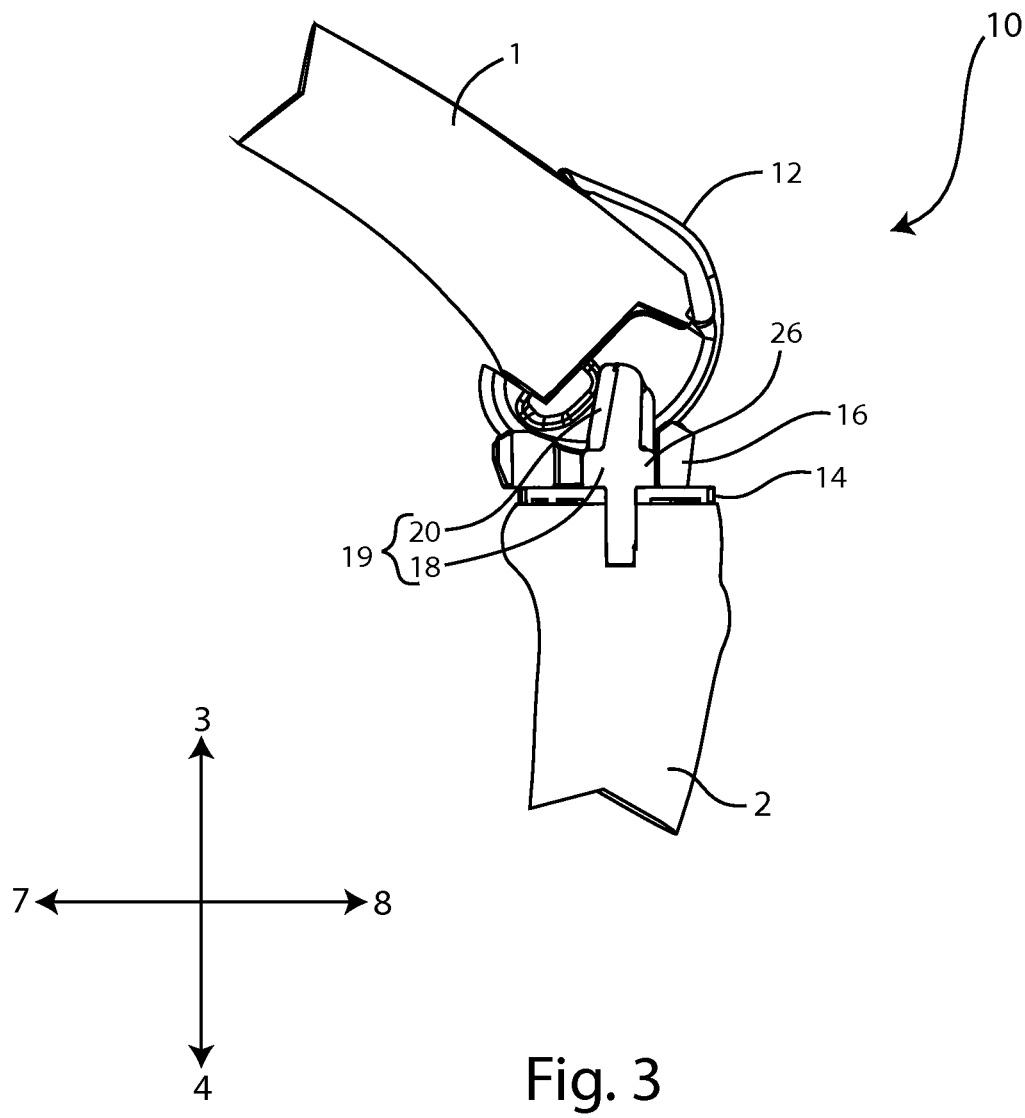
FIG. 3 illustrates a cross sectional side view of the prosthesis of FIG. 1 with the femur, tibia, tibial implant, tibial insert, femoral implant, and the cam post with the outer sleeve.

Referring to FIGS. 2 and 3, the prosthetic knee 10 comprises the tibial baseplate 14, attached to the resected tibia 2, a cam post 19 may be attached to the tibial baseplate 14 and may either be a modular or non-modular part of the baseplate. The cam post 19 helps guide the rotation of the femoral component and tibial insert 16 during flexion of the prosthetic knee 10. The cam post 19 of this embodiment is of two-piece construction, with a metallic cam post core 18 and a polymer outer wear sleeve 20. However, either the cam post core 18 or the sleeve 20 may be comprised of other biocompatible materials. A tibial insert 16 may be rotationally connected to the tibial baseplate 14, rotating about an axis within a tibial insert channel 26 which axis of rotation is medial to the midline of the tibia. A femoral implant 12 may be attached to a resected femur 1, which is supported by the tibial insert 16 and which slidably engages with the cam post 19 to guide the rotation of the tibial insert and posterior movement of the femoral component 16 during flexion of the prosthetic knee 10.

For any of the parts of the prosthetic knee any biocompatible material may be used, including but not limited to stainless steels, titanium and its alloys, cobalt-chrome and its alloys, ceramics, composite materials, and polymers.

Figure 4:
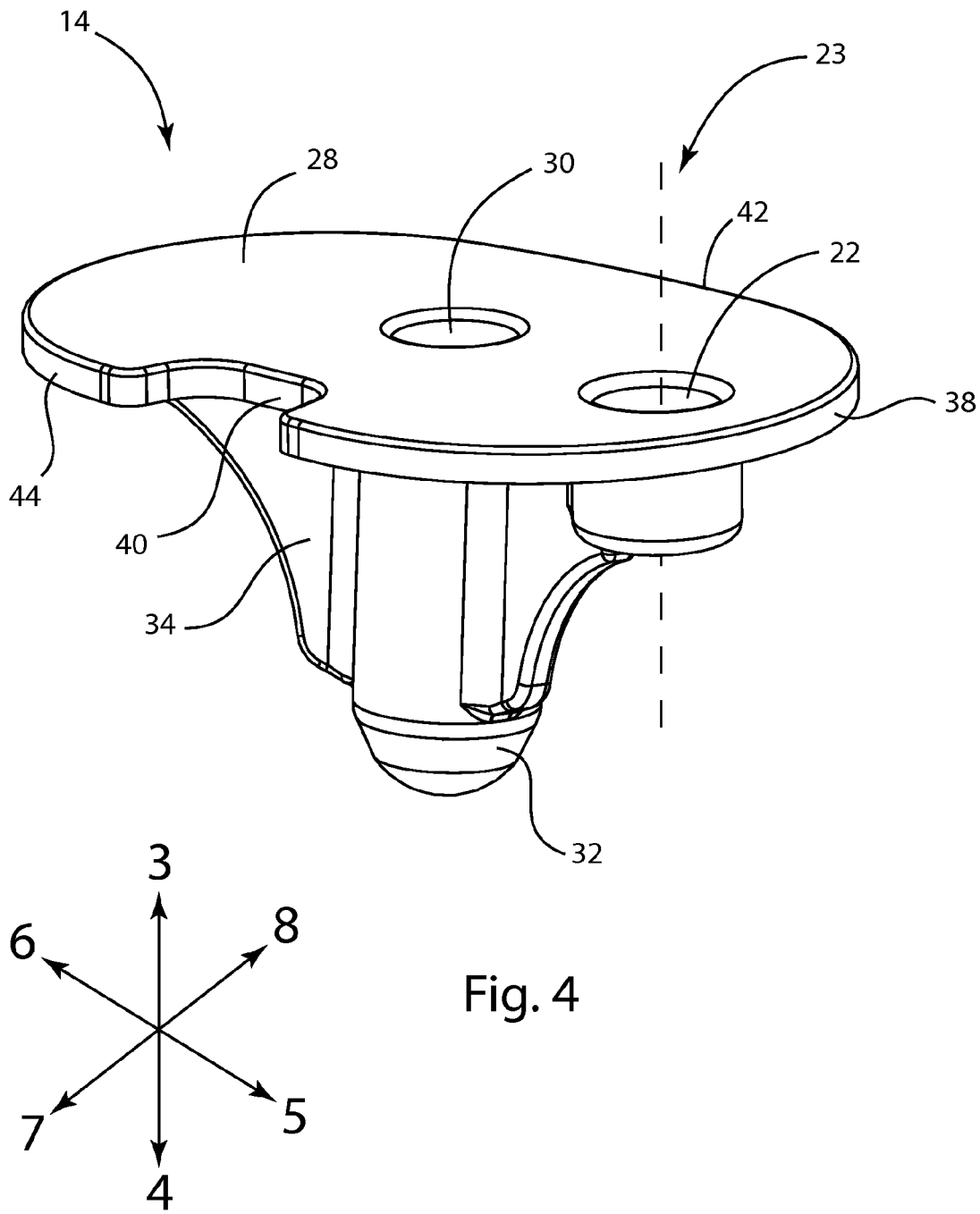
FIG. 4 illustrates a perspective top view of one embodiment of the tibial baseplate of FIG. 1 with the tibial baseplate cavity for retention of a boss of the tibial insert, and a tibial baseplate hole for passage of the cam post, on a tibial baseplate bearing surface, a keel extending into the tibia and at least one wing.
Figure 5:
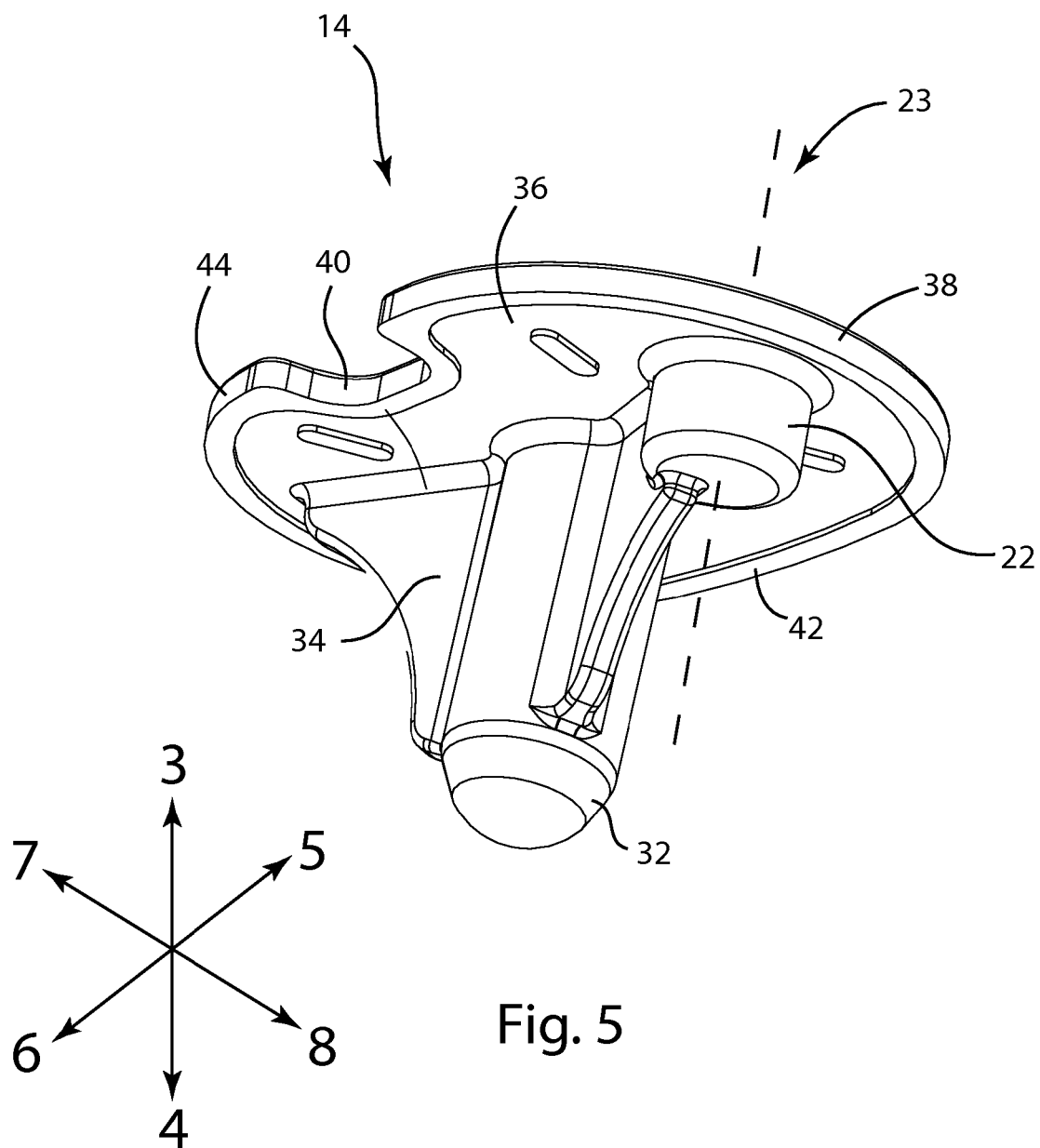
FIG. 5 illustrates a perspective bottom view of the tibial baseplate of FIG. 4 with the at least one wing, the keel, the tibial baseplate aperture and the tibial baseplate cam post aperture.

Referring to FIGS. 4 and 5, the tibial baseplate 14 may be made of a cobalt-chromium alloy. Other metals, such as titanium alloys or other composites may be used as well as polymer, ceramic, or other composite materials. In this embodiment the tibial baseplate 14 is rigidly attached to the resected tibia 2 on a tibia facing surface 36. Protruding inferiorly from the tibia facing surface is a keel 32 and at least one peg 35. The keel 32 may be driven into the core of the resected tibia 2. The at least one baseplate wing 34 extending from the tibia facing surface the length of the keel 32 and in communication with the keel may also be driven into the resected tibia 2 for added fixation and stabilization. Attachment of the tibial baseplate 14 may also be made by using cement, force fit, bone in-growth, bone screws or other method known in the art. A superior surface 28 of the tibial baseplate 14 may be substantially flat and acts as a support for the tibial insert 16. The superior surface 28 of the tibial baseplate 14 may be polished to minimize wear between the tibial baseplate 14 and the tibial insert 16. The tibial baseplate 14 includes a hole 30, for the mounting of cam post 19, which may be positioned substantially in the geometric center of the tibial baseplate 14 and is deep enough to receive at least a portion of the cam post 19. The tibial baseplate may also include a cavity 22 apart from the hole 30 and positioned substantially medial from the geometric center and apart from a periphery 38 of the tibial baseplate 14. The cavity 22 may provide a rotational medial axis 23 for the tibial insert 16 allowing for rotational movement of the tibial insert along that medial axis. In this embodiment, along a posterior side 44, opposite an anterior side 42, of the periphery 38 of the tibial baseplate 14 comprises a tibial baseplate notch 40 which may allow room for retention of the posterior cruciate ligament (PCL) or another ligament behind the plate 14.

Referring to FIG. 5, a perspective view illustrates the tibia-facing side 36 of the tibial baseplate 14. The keel 32 and the at least one baseplate wing 35 may comprise porous material that encourages bone in-growth.

Figure 6:
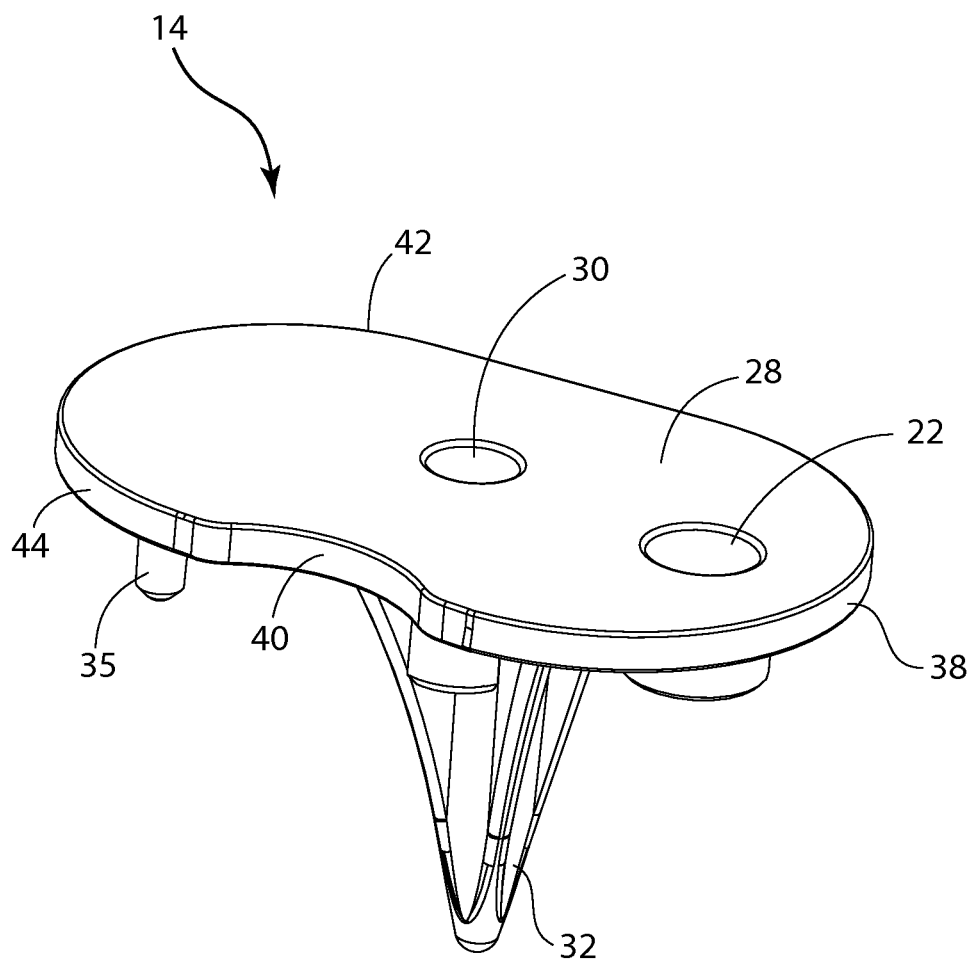
FIG. 6 illustrates a perspective top view of a different embodiment of the tibial baseplate of FIG. 1 with the tibial baseplate aperture and a tibial baseplate cam post aperture on a tibial baseplate bearing surface, a keel and at least one peg.
Figure 6:
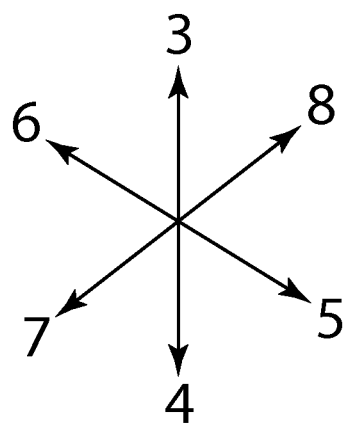
Figure 7:
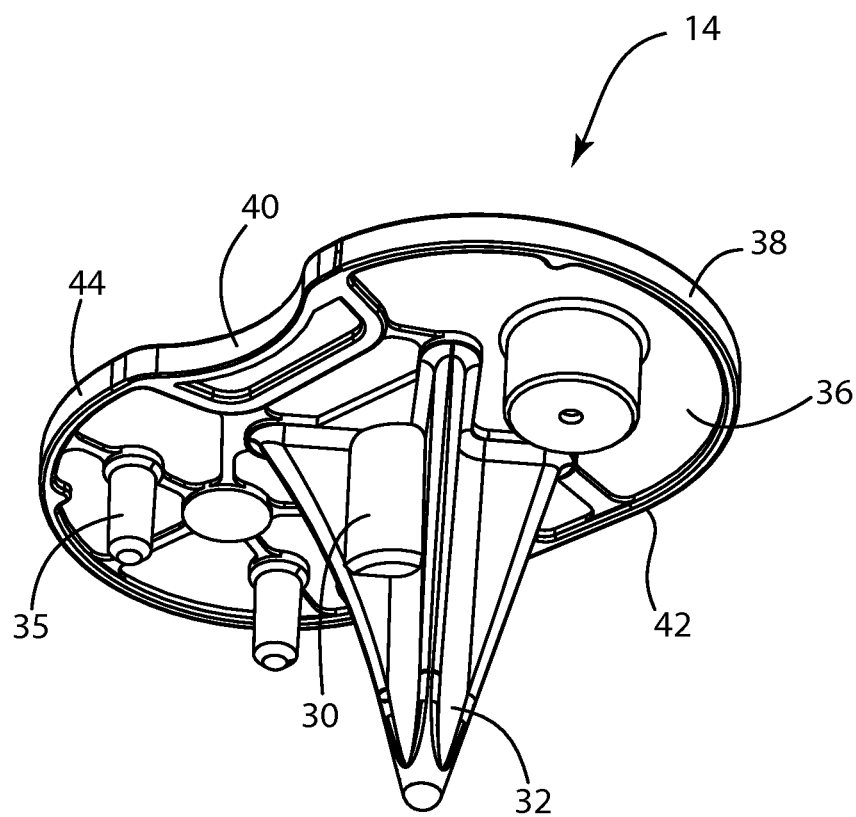
FIG. 7 illustrates a perspective bottom view of the tibial baseplate of FIG. 6 with the at least one peg, the keel, the tibial baseplate aperture and the tibial baseplate cam post aperture.
Figure 7:
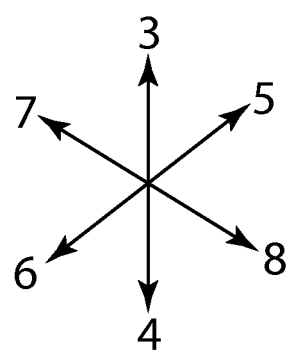

Referring to FIGS. 6 and 7, an alternate embodiment of the keel 32 is present with at least one peg 35. In this and other embodiments of the invention the size, shape and placement of the keel 32 may vary. The pegs 35 may not need to be present at all. Likewise, the tibial baseplate notch 40 can vary in size, shape and placement as well.

Figure 8:
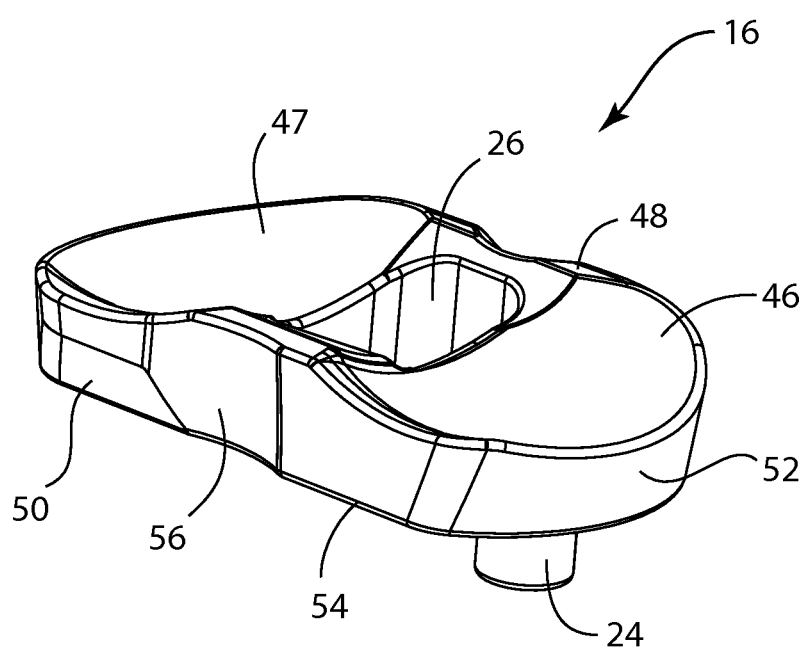
FIG. 8 illustrates a perspective top view of the tibial insert of FIG. 1 with articulating surfaces, a tibial insert notch on the posterior side to allow retention of the posterior cruciate ligament (PCL), a boss and a tibial insert channel.
Figure 8:
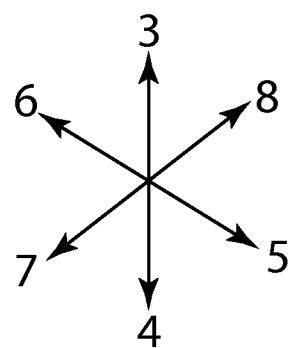

Referring to FIG. 8, the tibial insert 16 comprises a tibial baseplate facing side 54, a femoral implant facing side 55, a tibial insert periphery 52 extending around the tibial insert 16 and a tibial insert channel 26. The tibial insert channel 26 may be arc-like shaped and may be generally centrally located extending from the femoral implant facing side 55 to the tibial baseplate facing side 54 and is shaped to slidably fit over the cam post 19. The tibial channel 26 is large enough and shaped to allow some arc-like rotation of the tibial insert 16 after being positioned over the cam post 19. The femoral implant facing side 55 may comprise a first articulating surface 46 and a second articulating surface 47 positioned opposite the tibial insert channel 26. The first articulating surface 46 may be positioned substantially medial to the insert channel 26 and extend from the insert channel 26 to the tibial insert periphery 52. The second articulating surface 47 may be positioned substantially lateral to the insert channel 26 and extend to the tibial insert periphery 52. The articulating surfaces 46, 47 are shaped and curved to align with the femoral implant 12 for when the prosthetic knee 10 is implanted in the patient.

Figure 9:
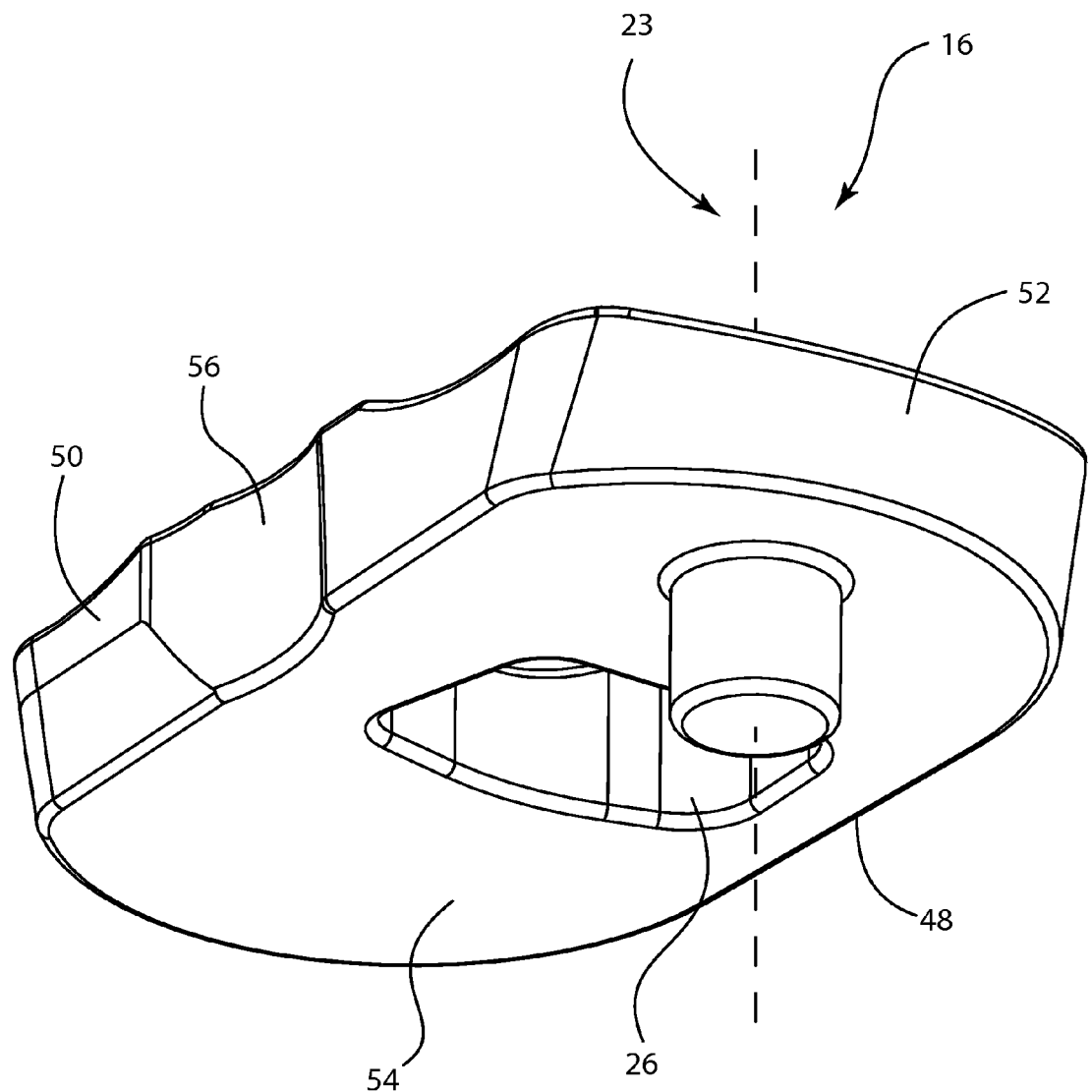
FIG. 9 illustrates a perspective bottom view of the tibial insert of FIG. 8 with the tibial insert channel, the boss, the tibial insert notch, a baseplate facing surface and an axis of rotation generally in the center of the boss.
Figure 9:
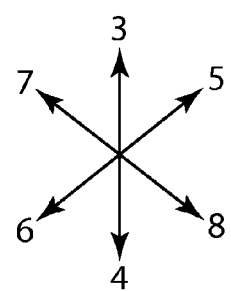

Referring to FIG. 9, the tibial baseplate facing side 54 may be substantially flat with the exception of a boss 24 extending inferiorly, positioned toward the medial side of the tibial baseplate 16 but apart from the tibial insert periphery 52. The flat tibial baseplate facing side 54 may align with the flat superior surface 28 of the tibial baseplate 14 and the boss 24 being is positioned within the cavity 22 of the tibial baseplate 14. The cavity 22 provides a rotation axis of the tibial insert 16 allowing for some amount of pivot rotation along this rotation axis which allows the tibial insert to perform an arc-like rotation in relation to the tibial insert channel 26 and the cam post 19. The rotation of the tibial insert 16 is constrained by the tibial insert channel 26 positioned over the cam post 19.

The tibial insert 16 can be comprised of many biocompatible materials. Polymers may be preferred but metals and ceramics may also be used.

Figure 10:
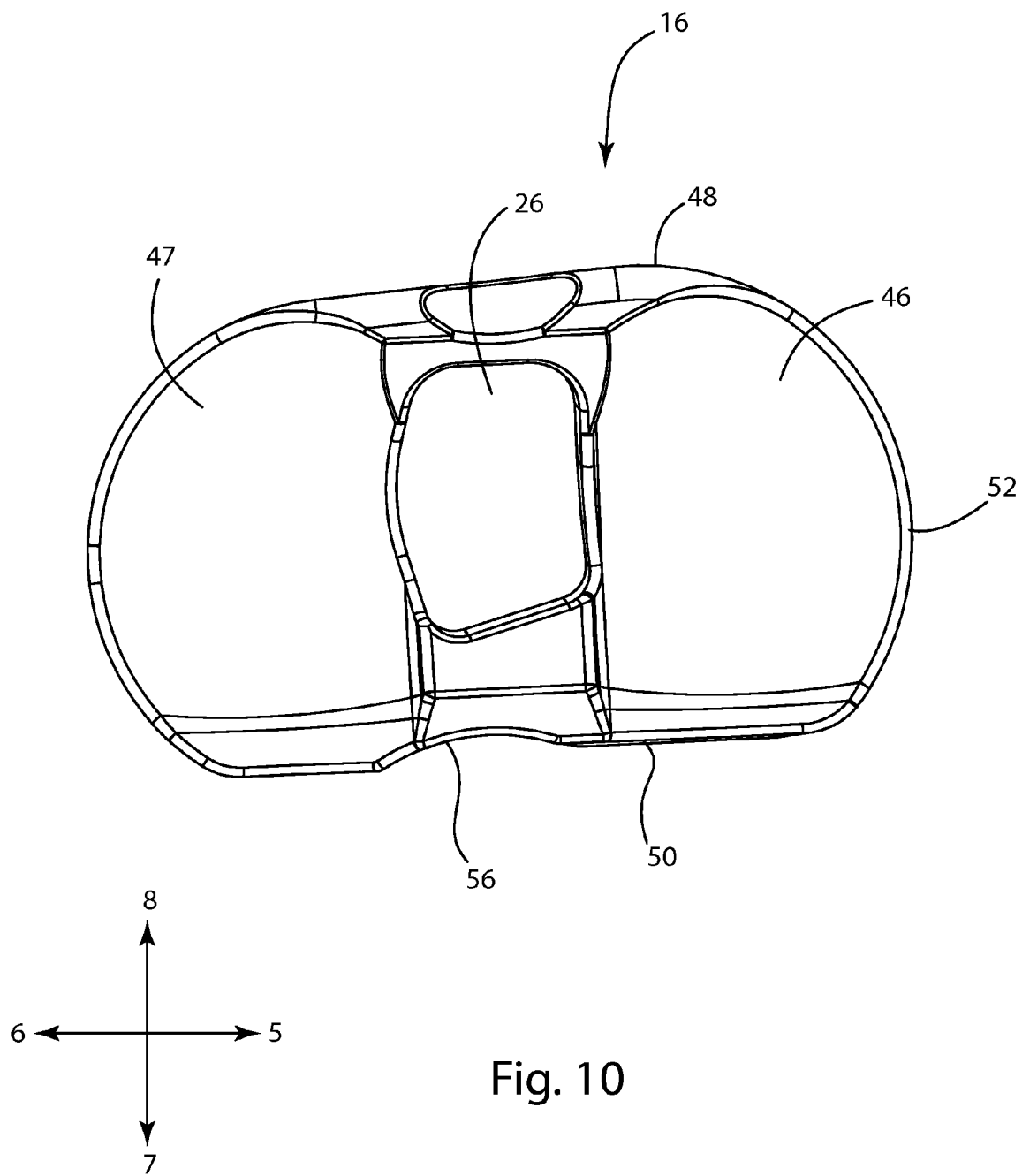
FIG. 10 illustrates a top view of the tibial insert of FIG. 8 with the articulating surfaces, the notch and the channel.

Referring to FIG. 10, a tibial insert notch 56 may be positioned along the tibial insert periphery 52 toward the posterior end of the tibial insert 16. The tibial insert notch 56 may be aligned with the tibial baseplate notch 40 and may allow room for retention of the posterior cruciate ligament (PCL) or another ligament behind the tibial baseplate 14 and the tibial insert 16.

Figure 11:
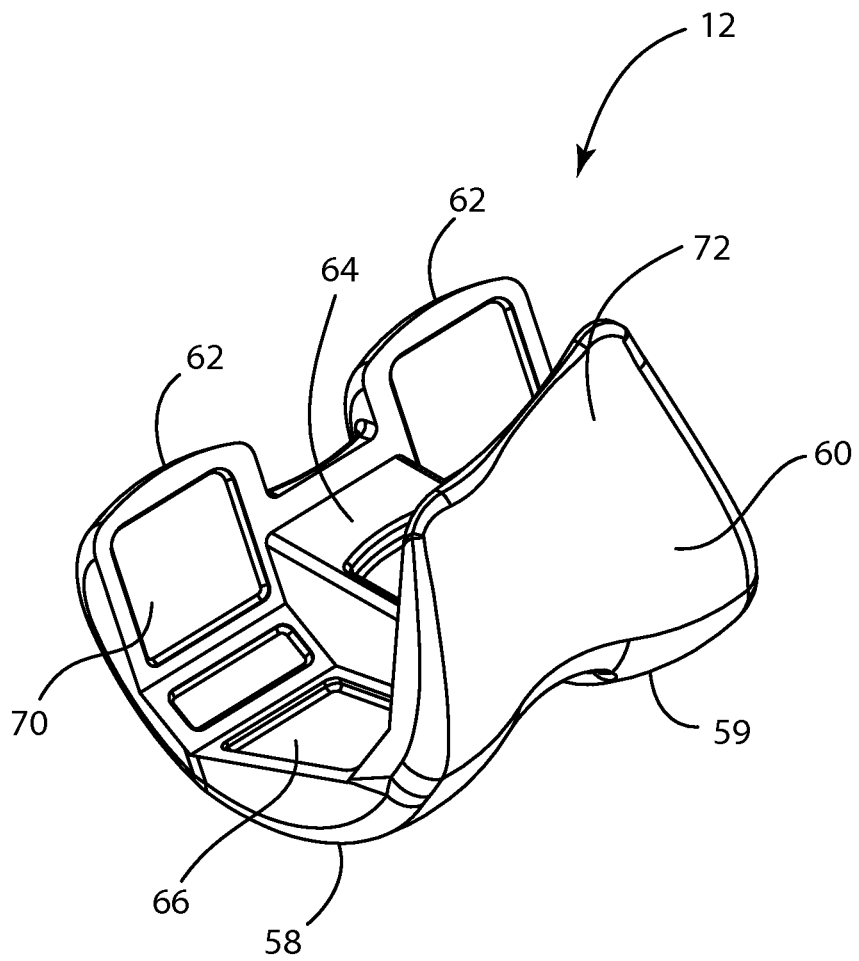
FIG. 11 illustrates a perspective front view of the femoral implant of FIG. 1 with condyles for articulation with the tibial baseplate, a cam feature for interaction with the cam post and a trochlear notch.
Figure 11:
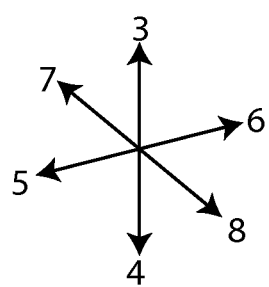

Referring to FIG. 11, the femoral implant 12 has a bone-facing side 70, a trochlear groove 72 on an anterior end 60 end of the femoral implant 12, and a cam feature 64. The trochlear groove 72 adjoins a first condyle 58 and a second condyle 59 extending posteriorly to a posterior end 62 of the femoral implant 12. The cam feature also adjoins the first and second condyles 58, 59. The first condyle and second condyles 58, 59 may curve cephalically, to match the contours of a natural distal end of a femur and are shaped to align with the first articulating surface 46 and the second articulating surface 47 of the tibial insert 16 respectively. The radius of curvature of the condyles 58, 59 may relatively match the same curvature of the articulating surfaces 46, 47 of the tibial insert 16. The condyles 58, 59 may be polished to minimize wear between the condyles 58, 59 and the articulating surfaces 46, 47 of the tibial insert 16. If the tibial insert 16 is also made of metal, including those metals named herein, it may also be polished to minimize wear.

The bone-facing side 72 may have a bone-facing surface 66 which may comprise a porous material to encourage bone in-growth. A gap 68 between the condyles 58, 59 is generally a fixed height, but the condyles 58, 59 may be of various widths, sizes and curvatures depending on the specific anatomy of the patient or tibial insert 16. The surface curvature of the condyles 58, 59 may also vary to match the curvature of the specific tibial insert 16 chosen for the patient's mobility requirements.

Figure 12:
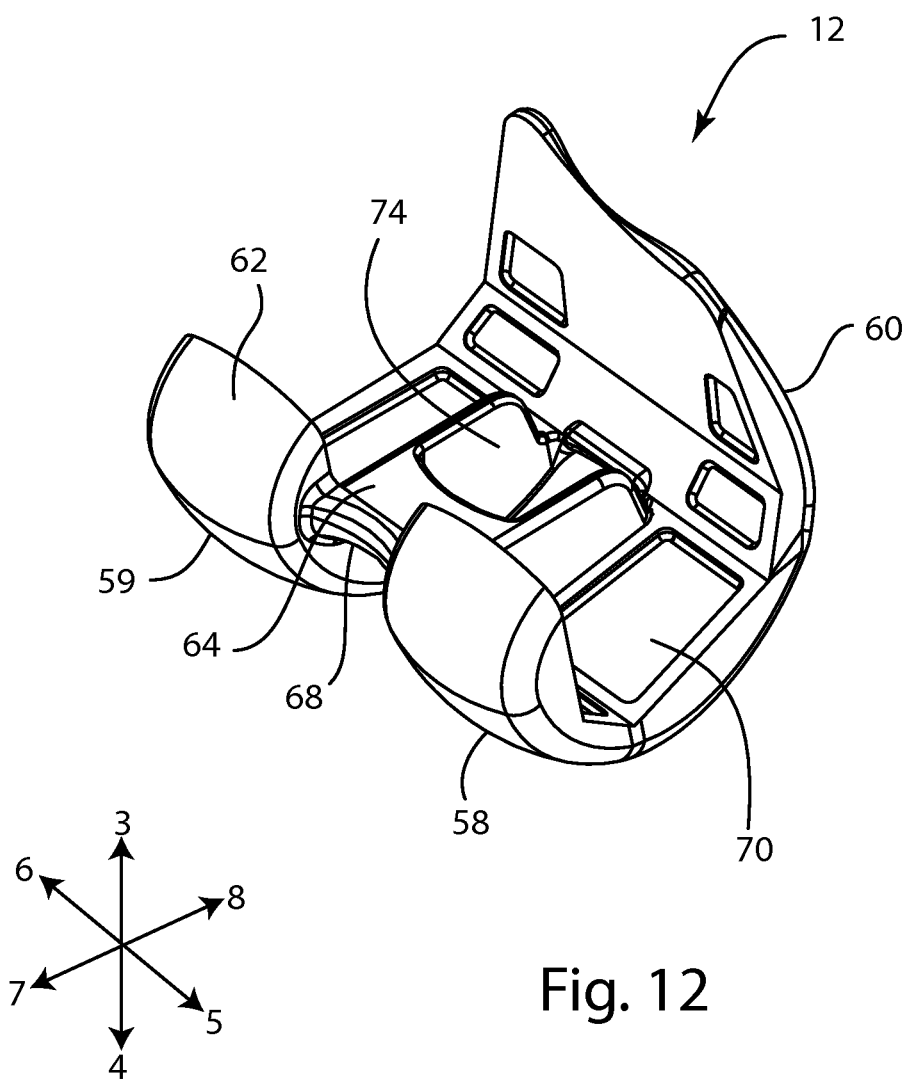
FIG. 12 illustrates perspective back view of the femoral implant of FIG. 11 with a femoral implant opening for engagement with the cam post, a condyle gap between the condyles and condyles.

Referring to FIG. 12, the femoral implant 12 may further comprise an opening 74 shaped and positioned to receive the cam post 19. The cam post 19 slidably inserts into the opening 74 and a posterior side of the cam post 19 engages the cam feature 64 on an anterior side of the cam feature 64 during knee flexion.

Figure 13:
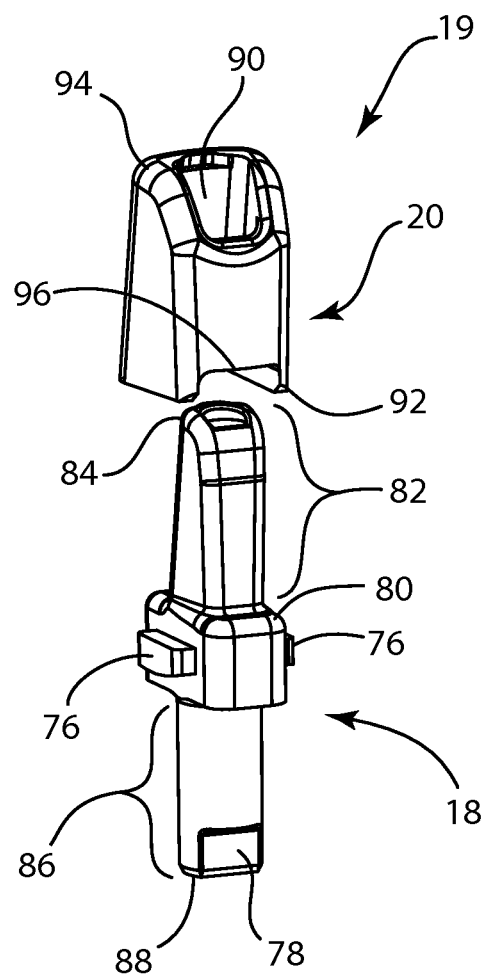
FIG. 13 illustrates an exploded perspective view of the cam post of FIG. 2 with a cam post core and an outer sleeve.
Figure 13:
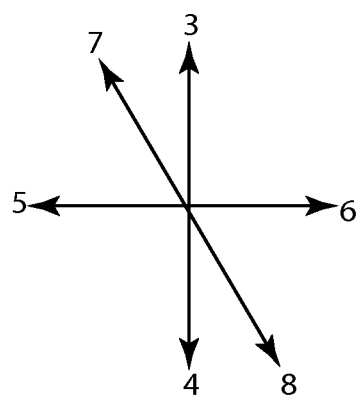

Referring to FIG. 13, the cam post 19 has the cam post core 18 and the outer sleeve 20. The cam post core 18 has an inferior end 88, a superior end 84, a superior portion 82, an inferior portion 86 and an intermediate portion 80 between the superior and inferior portions 82, 86. The intermediate portion 80 may of greater width than the inferior and superior portions 82, 86, and may comprise wings 76 extending laterally and medially and are positioned as a stop to engage the outer sleeve 20. Toward the inferior 88 the cam post core may have a Morse taper or similar taper or pin which engages in the tibial baseplate hole 30 and a core notch 78 which may act like a key fit. The intermediate portion may also vary in height (superiorly to inferiorly) depending on variations of the patients anatomy.

Figure 14:
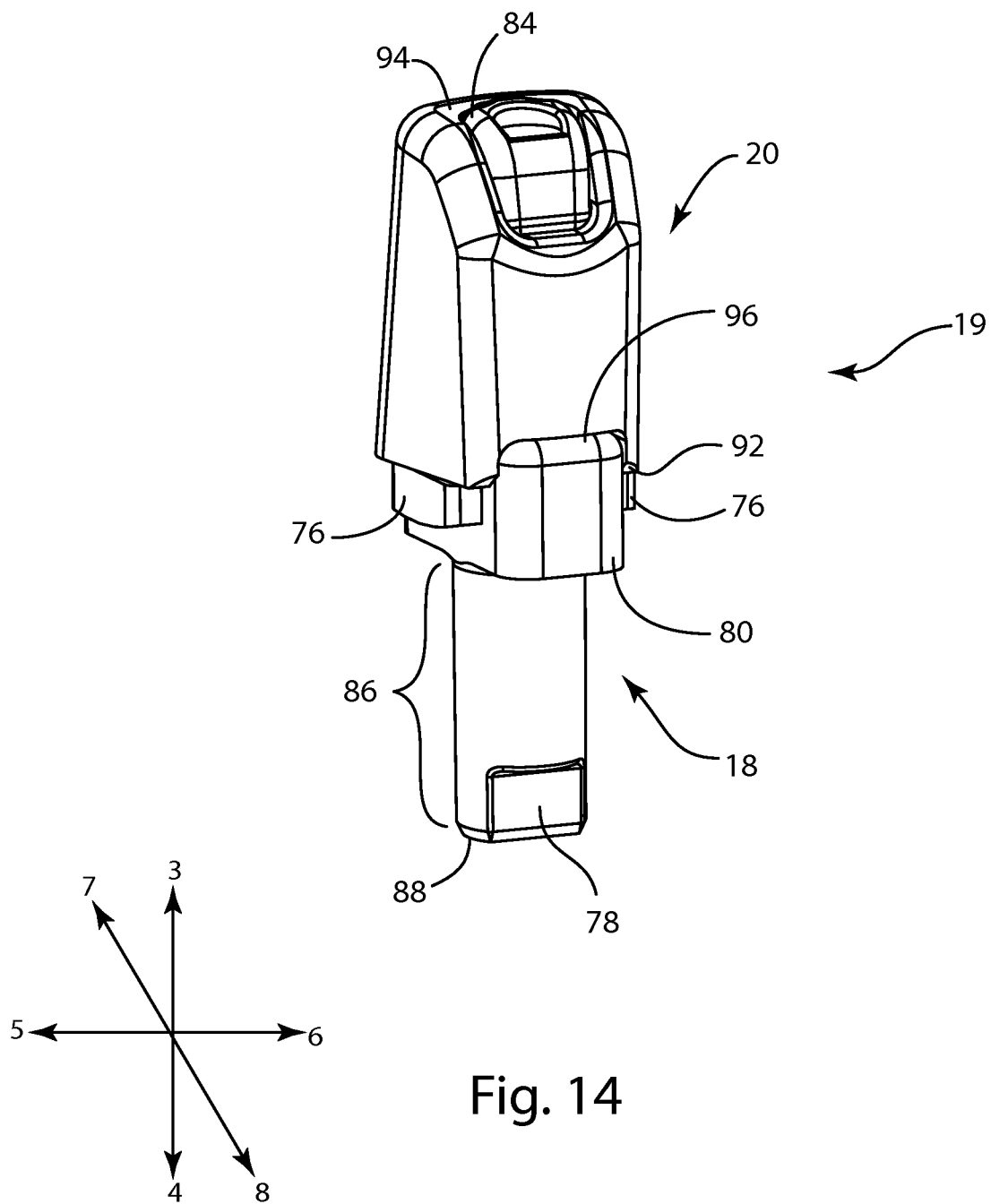
FIG. 14 illustrates the cam post of FIG. 13 with the outer sleeve at least partially encircling the cam post core.

Referring to FIGS. 13 and 14, the superior portion 82 is shaped to slidably receive the outer sleeve 20. The outer sleeve 20 has a sleeve channel 90, a superior end 94 and an inferior end 92. The sleeve channel 90 is shaped to slide over the superior portion 82 at least partially surrounding the superior portion 82. The outer sleeve is positioned around the superior portion 82 and slides onto the superior portion 82 until the sleeve inferior end 92 engages the wings 76 of the intermediate portion 80 of the cam post 19. The outer sleeve 20 may comprise a sleeve notch 96 toward the inferior end 92 of the outer sleeve 20 which may communicate with the intermediate portion 80 and receive a portion of the intermediate portion 80 within the sleeve notch 96, providing greater stability and fixation of the cam post core 18 to the outer sleeve 20. The sleeve notch 96 may also provide rotational stops so the sleeve is unable to rotate when snapped into engagement with the cam post core 18. The outer sleeve 20 may be secured to the cam post core 18 through snap fit features. After the outer sleeve 20 is positioned around the superior portion 82 of the cam post core 82 the cam post core superior end 84 and the outer sleeve superior end 94 may be flush.

The cam post core 18 may be made of cobalt-chrome or its alloys, titanium or its alloys, stainless steel or any other biocompatible metal, ceramic or polymer. The outer sleeve 20 may be preferably made of polymer; however, it may also be comprised of many other biocompatible materials including ceramics and metals. In addition the cam post core 18 and the sleeve 20 may be one piece instead of two pieces.

Referring back to FIG. 3, the tibial baseplate 14 is secured to the resected tibia 2. The cam post 19 may be secured to the tibial baseplate 14 using a Morse taper or similar taper or pin feature (the core notch 78 of the cam post core 18). The tibial insert 16 is positioned over the cam post 19 and the boss 24 of the tibial insert 26 is positioned within the cavity 22 of the tibial baseplate providing an axis of rotation 23. The tibial insert channel 26 may contain a metal band lining the channel 26. The sleeve 20 of the cam post 19 may be polyethylene and may extend from the sleeve superior end 94 to the tibial baseplate 14 when the cam post 19 is correctly positioned in the baseplate 14. This feature of the metal band and extension of the polyethylene sleeve 20 may minimize stresses on the tibial insert 16 when it contacts the cam post 19 and stops.

The femoral implant 12 is secured to the resected femur 1. The cam post is then positioned within the opening 74 of the femoral implant 12 engaging the cam feature 64 during knee flexion. The cam feature 64 provides rollback and femoral external rotation during knee flexion. The cam post 19 after engaging the cam feature 64 allows two fully guided rotational axes and provides anterior and posterior stabilization features. The cam post 19 engages the cam feature 64 resisting posterior tibial translation. The cam post 19 also engages the tibial insert channel 26 to restrict anterior displacement of the tibial insert and the tibia as well.

One fully guided rotational axis is between the femoral implant 12 and the tibial insert 16 by engagement of the condyles 58, 59 with the articulating surfaces 46, 47. A second fully guided rotational axis is between the tibial insert 16 and the tibial baseplate 14 by aligning the tibial baseplate facing side 54 with the flat superior surface 28 of the tibial baseplate 14. The second rotational axis is accomplished by the positioning of the boss 26 within the cavity. The first and second rotational axes closely match the motion of the natural knee and are suitable for hard-on-hard bearing contact surfaces, such as the use of cobalt-chrome, ceramic, composite or other hard materials for the femoral implant 12, tibial insert 16 and tibial baseplate 14, which may lead to longer durability of the prosthetic knee. The potential advantage of using exclusively hard materials is that polyethylene debris can be eliminated and wear particle generation can be reduced, reducing the chance of osteolysis and implant loosening. However, to be able to use exclusively hard materials requires a fully guided motion conforming mobile bearing design— meaning a design in which relative motion between any two parts occurs along only one path.

Cobalt-chrome and its alloys are not the only hard-on-hard material that may be used, other examples include, but are not limited to, stainless-steel, titanium and its alloys, titanium carbide, titanium nitride, ion-implantation of titanium, diffusion hardened metals, diamond like coatings, diamond-like carbon, zirconium nitride, niobium, oxenium or oxidized zirconium, ceramics such as alumina and zirconia, and many other biocompatible materials and coatings.

Another advantage of the features recited herein is that this design provides knee motion during flexure closer to the natural knee. Two other benefits of these novel features is that (1) the cam post 19 can provide both anterior and posterior rotational stops for the tibial insert 16, and (2) the cam post 19 can independently provide anterior and posterior translation stops for the femoral implant 12. These benefits of the design contribute to the overall stability of the prosthetic knee, eliminates the risk of bearing spin out, and limits anterior tibial translation which is provided by the anterior cruciate ligament in the normal knee 10.

In alternative embodiments, the various components shown and described herein may have different sizes, configurations (such as size of the keel, shape and size of the cam post, the width of tibial insert, and the like) material properties, and other variations to adapt them to variations in patient anatomy. If desired, multiple versions of each of the femoral implant, tibial baseplate, and tibial insert components may be provided together in a single kit to enable a surgeon to interoperatively select the best set of components for a patient.

Figure 15:
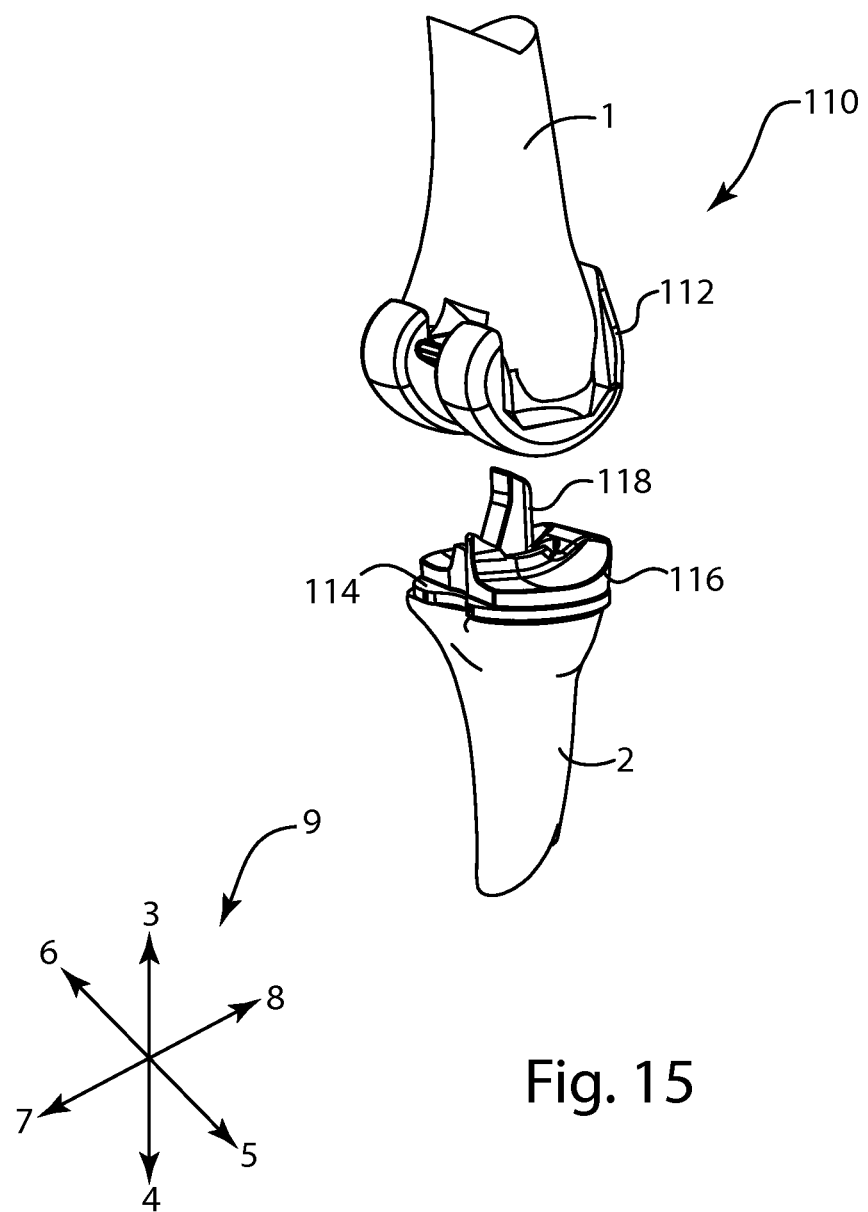
FIG. 15 illustrates a perspective view of an alternate embodiment of the prosthesis with a femur, a tibia, femoral implant, a cam post a tibial insert and a tibial baseplate.

Referring to FIG. 15, an alternate embodiment of a prosthetic knee 110 includes a, a femoral implant 112, a tibial baseplate 114, a tibial insert 116 and a cam post 118. The interaction between each of the components is similar to the previous embodiment.

Figure 16:
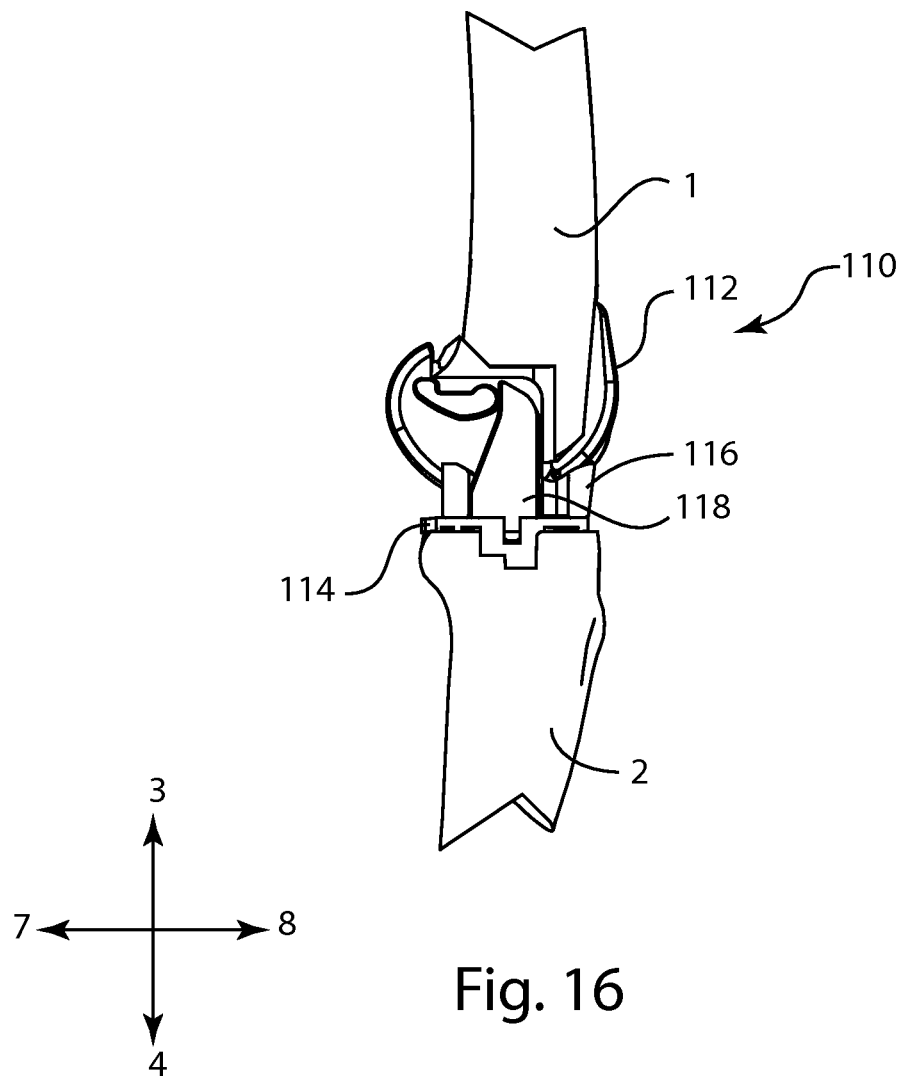
FIG. 16 illustrates a cross sectional side view of the prosthesis of FIG. 15 with the femoral implant the cam post, the tibial insert and the tibial baseplate.

Referring to FIG. 16, similar to the previous embodiment the femoral implant 112 engages the tibial insert 116 and the cam post 118 may engage a cam feature 120 during flexion of the knee providing anterior and posterior translational stops for the femoral implant. The cam 118 post is fixed to the tibial baseplate 114 and passes through a tibial insert channel 130 (better depicted in FIGS. 19 and 20). The cam post 118 provides anterior and posterior rotational stops for the tibial insert 116.

Figure 17:
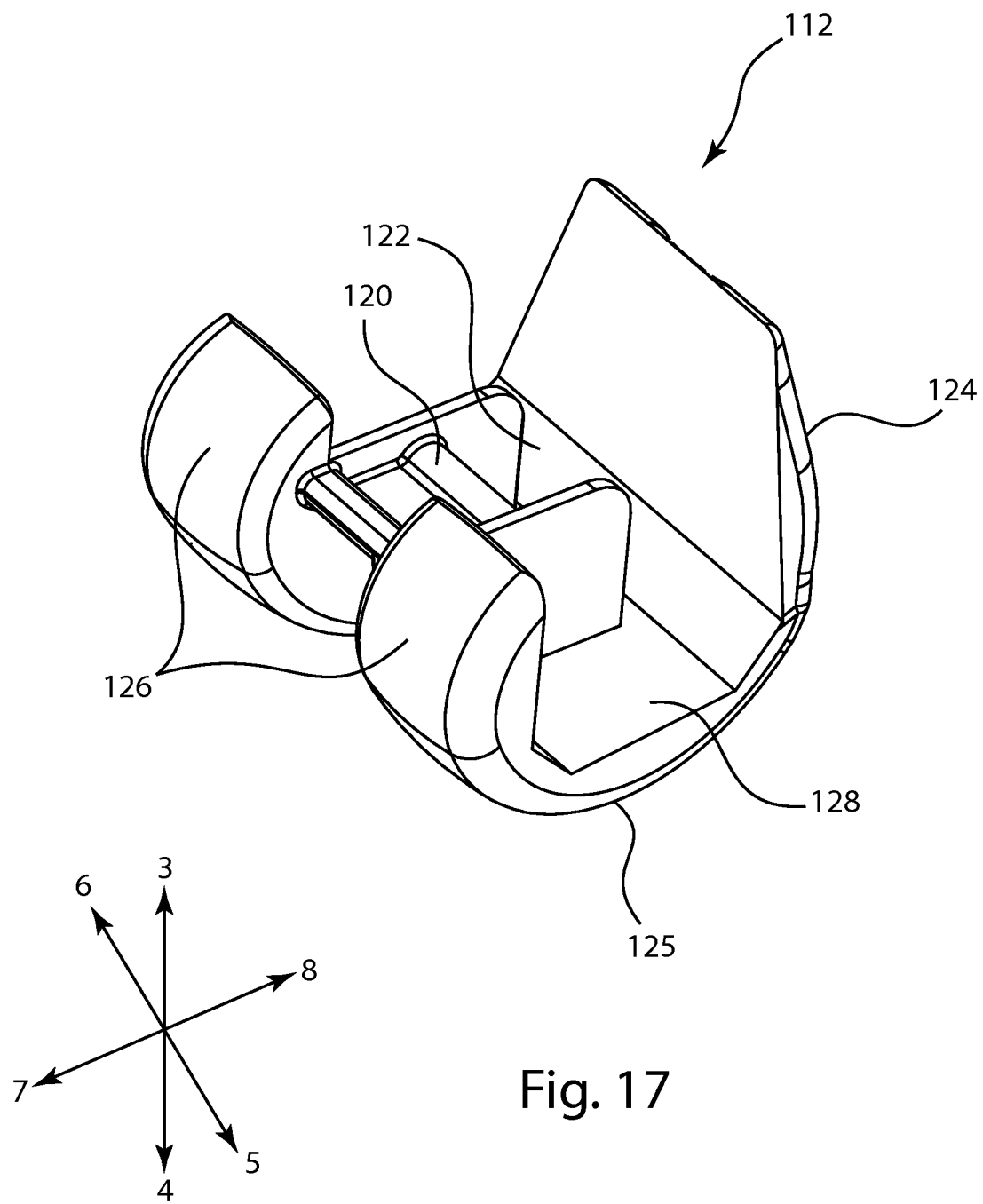
FIG. 17 illustrates a perspective back view of the femoral implant of FIG. 15 with a cam feature, condyles, and a femoral opening.

Referring to FIG. 17, the femoral implant 112 includes condyles 125 which interact with and are highly conforming with the tibial insert 116. The femoral implant also includes a bone facing side 128 that is configured to engage a resected femur. Between an anterior end 124 and a posterior end 126 lies a femoral implant opening 122 shaped to receive the cam post 118 and immediately posterior to the opening 122 is a cam feature 120 which is positioned and shaped to engage the cam post 118 during flexion of the prosthetic knee 110. The cam feature 120 provides rollback and femoral external rotation during knee flexion.

Figure 18:
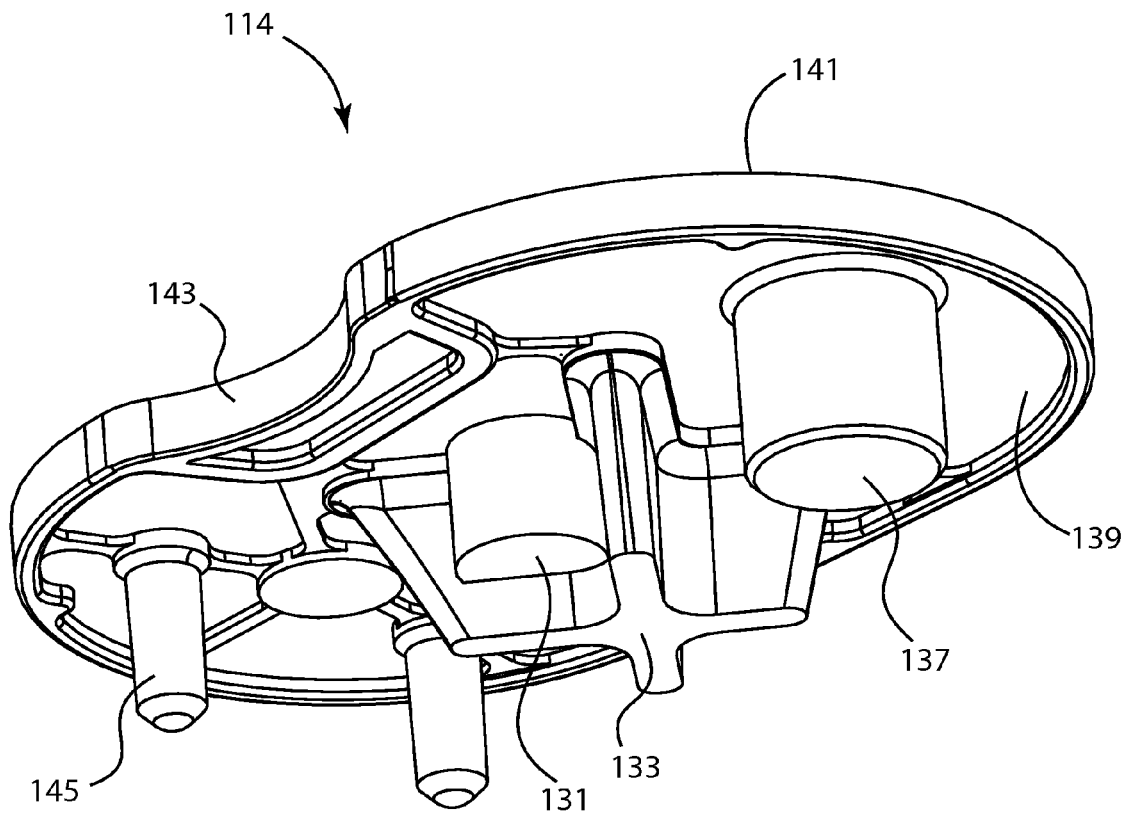
FIG. 18 illustrates a perspective bottom view of the tibial baseplate of FIG. 15 with a keel (smaller than the keels of FIGS. 4-7), at least one peg, a cavity to receive a boss of the tibial insert and tibial facing side and a notch on the posterior side for retention of the PCL.
Figure 18:
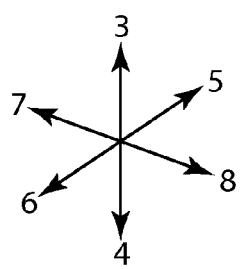

Referring to FIG. 18, the tibial baseplate 114 is similarly shaped to the previous embodiment's baseplate 14. However, a keel 133 may be shorter. The tibial baseplate 114 may comprise the same elements of the previous embodiment and they may carry out the same functions of the previous embodiment as well. The parts of the tibial baseplate which my mirror the previous embodiment include a tibial baseplate hole 131 to engage the cam post 18, a tibial baseplate cavity 137 to engage a boss 132 (depicted in FIG. 19), a tibia facing surface 137 configured to engage the resected tibia 2. The features may also include at least one peg 145 extending from the tibia facing surface 137 to engage the tibia 2. A tibial baseplate superior surface 141 is generally flat allowing for interaction with the tibial insert 116 similar to the previous embodiment. The tibial baseplate may also further comprise the tibial baseplate notch 143 which may allow room for retention of the posterior cruciate ligament (PCL) or another ligament behind the tibial baseplate 114 and the tibial insert 116.

Figure 19:
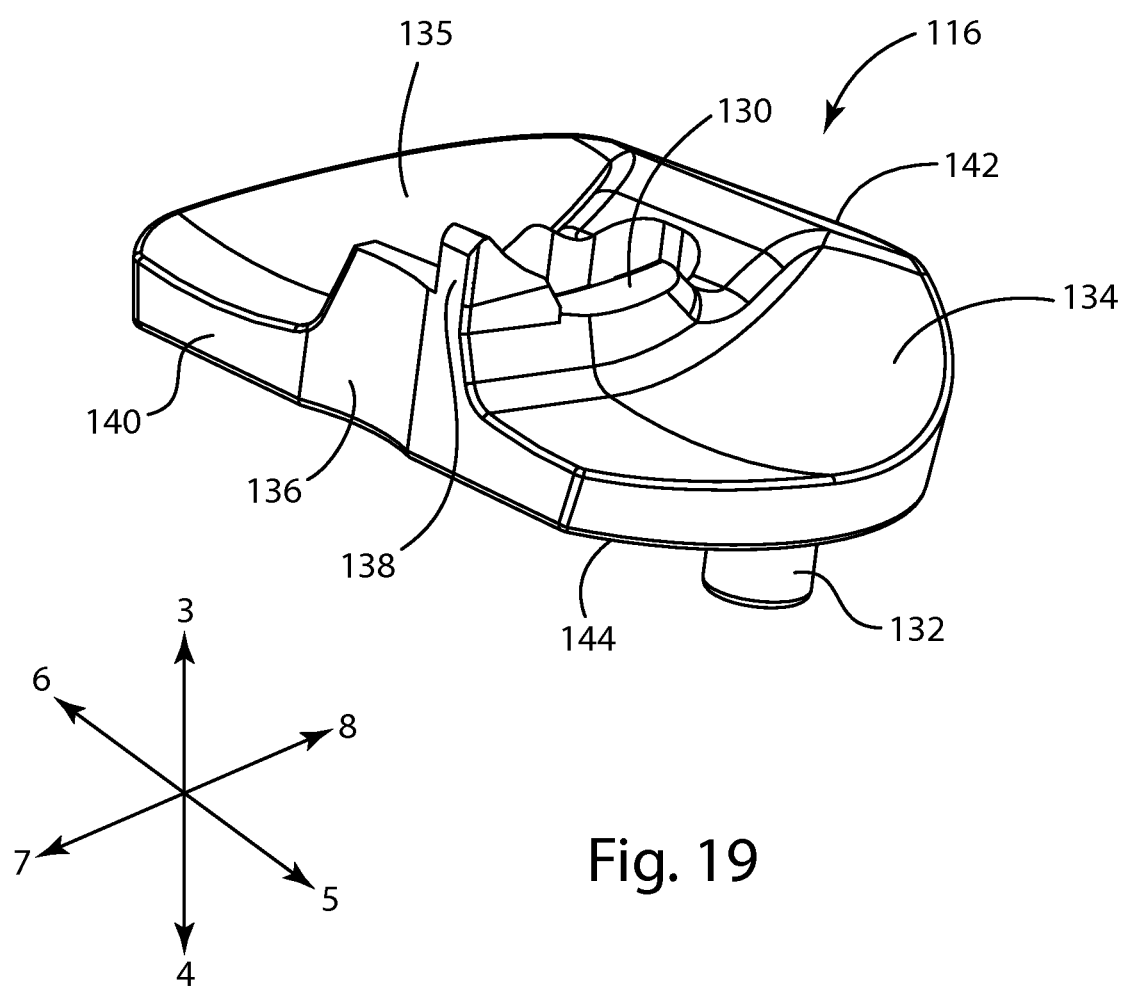
FIG. 19 illustrates a perspective top view of the tibial insert of FIG. 15 with articulating surfaces to interact with the condyles of the femoral implant of FIG. 17, a boss to interact with the cavity of the tibial baseplate of FIG. 18, a medial peak, a tibial insert channel for passage of the cam post, and a notch on the posterior side of the tibial insert for retention of the PCL.
Figure 20:
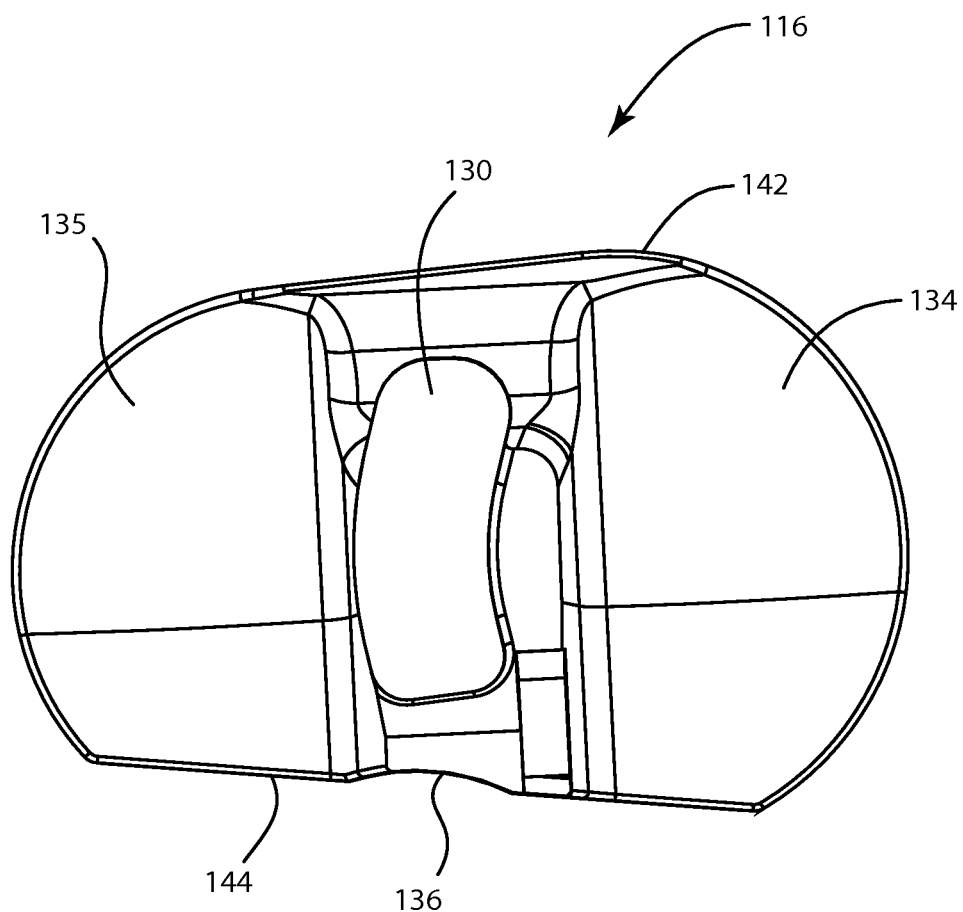
FIG. 20 illustrates a top view of the tibial insert of FIG. 19 with a channel, a notch and articulating surfaces.
Figure 20:
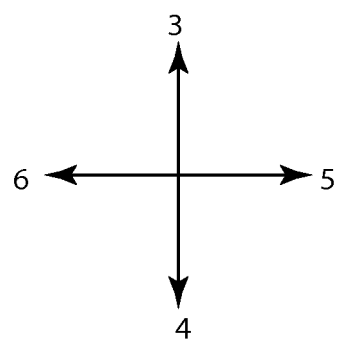

Referring to FIGS. 19 and 20, the tibial insert 116 may comprise many of the same elements with the same function and design as the previous embodiment. However, an anterior end 142 may have a greater width than a posterior end 140 of the tibial insert 116. In addition a peak 138 may extend superiorly and may be positioned toward the posterior end 140 of the tibial insert 116 to interact between, and are highly conforming with, the condyles 125 of the femoral implant 112. The other characteristics of the tibial insert 116 include a medial and a lateral articulating surfaces 134, 135 sculpted and curved to align with the condyles 125 of the femoral implant, as well as the tibial insert channel 130 which may be somewhat arc shaped (Refer to FIG. 17), which is large enough to slidably receive the cam post 118 and allows for anterior posterior rotation along the arced channel 130. Furthermore the tibial insert 116 includes the tibial insert baseplate facing surface 144 which is generally flat configured to align with the generally flat tibial baseplate superior surface 144, and the boss 132 shaped to align and be received within the cavity 137 to provide a rotational axis for the anterior posterior rotation of the tibial insert 116. The tibial insert 116 also includes the tibial insert notch 136 which may allow room for retention of the posterior cruciate ligament (PCL) or another ligament behind the tibial baseplate 114 and the tibial insert 116.

Figure 21:
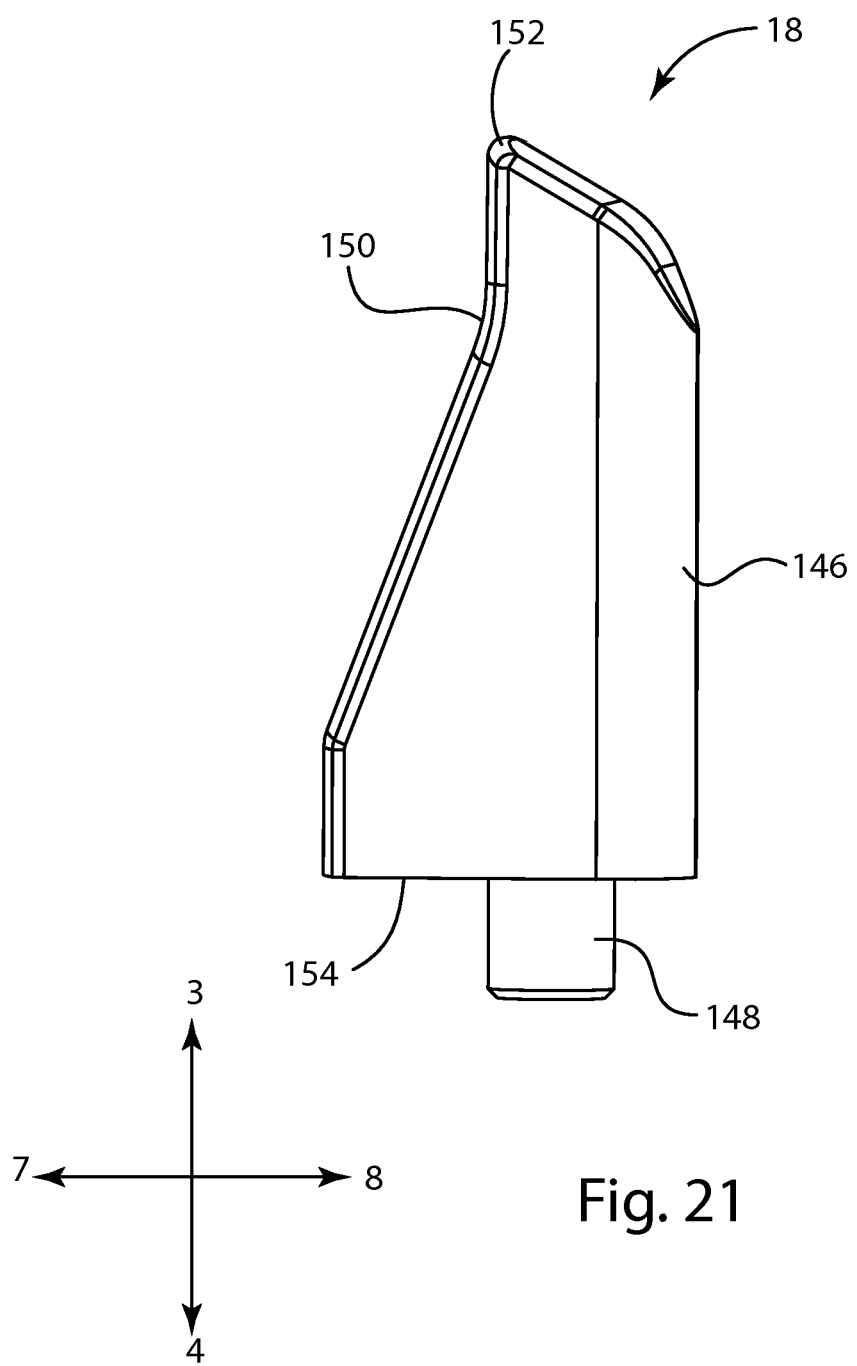
FIG. 21 illustrates a side view of the cam post of FIG. 15 with a cam post body superior end and an inferior end with a groove between the superior and inferior ends and a cam post boss extending inferiorly from the inferior end of the cam post.
Figure 22:
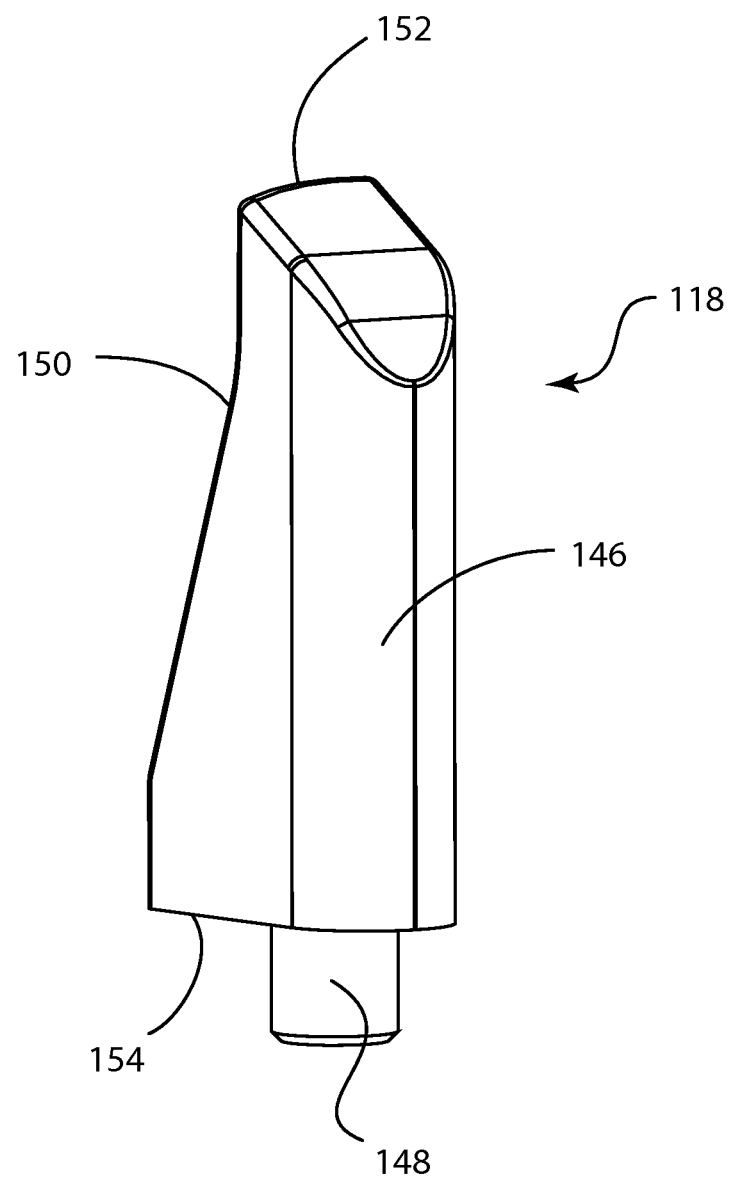
FIG. 22 illustrates a perspective front view of the cam post of FIG. 21.
Figure 22:
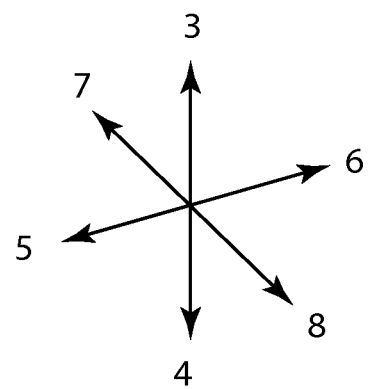

Referring to FIGS. 21 and 22, the cam post 118 includes a cam post body 146 with a wider inferior end 154 than a superior end 152 and a cam post boss 148 extending inferior shaped to engage the tibial baseplate hole_131. The cam post 118 is fixed to the tibial baseplate 114 through the interaction between the tibial baseplate hole 131 and the cam post boss 148.

The cam post 118 decreases in width from the inferior end 154 to the superior end 152. Between the superior end 152 and the inferior end 154 is a groove 150 shaped to engage the cam feature 120 of the femoral implant 112 during flexion of the prosthetic knee 110.

The interaction each of the components is generally similar to the previous embodiment with differences in structure only (refer to FIG. 13). The features recited herein are that this design provides knee motion during flexure closer to the natural knee. Benefits of these novel features include the same features as previously recited which are (1) the cam post 118 can provide both anterior and posterior rotational stops for the tibial insert 116, and (2) the cam post 118 can independently provide anterior and posterior translation stops for the femoral implant 112. These benefits of the design contribute to the overall stability of the prosthetic knee 110.

Figure 23:
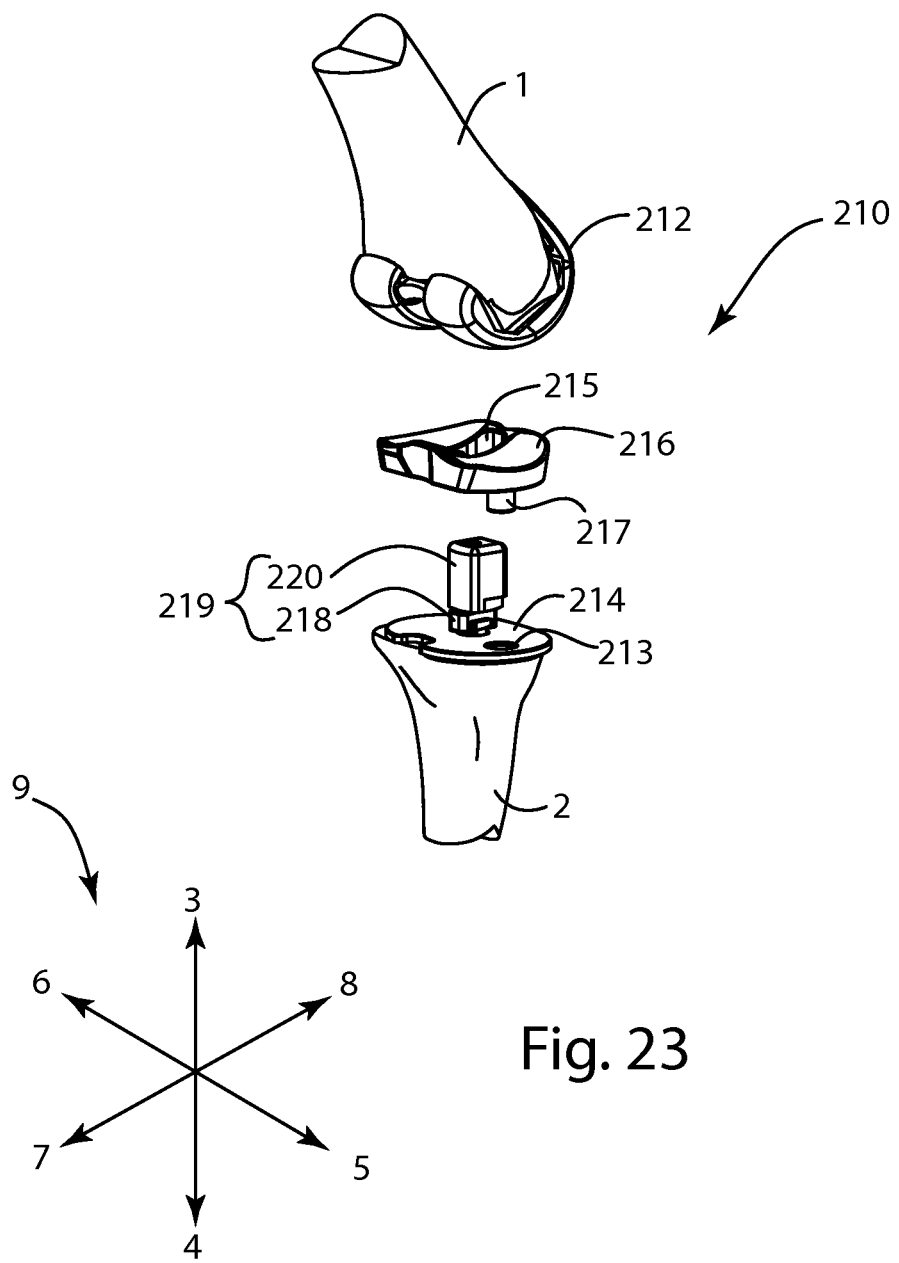
FIG. 23 illustrates an exploded perspective back view of an alternate embodiment of the prosthesis of FIG. 1 with a femur, a tibia, femoral implant, a cam post, a tibial insert and a tibial baseplate.
Figure 24:
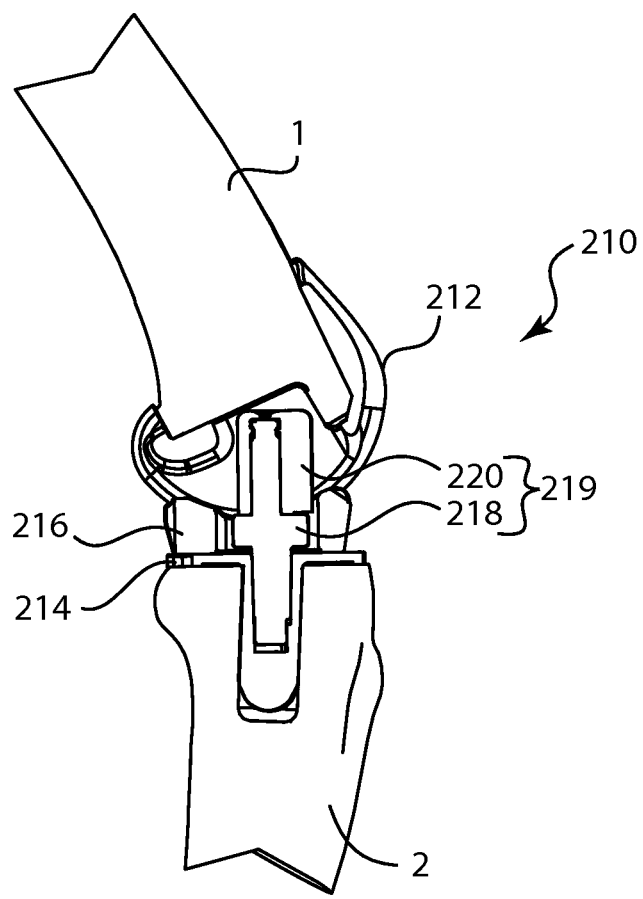
FIG. 24 illustrates a cross sectional side view of the prosthesis of FIG. 23 with a femoral implant, a cam post, a tibial insert and a tibial baseplate.
Figure 24:
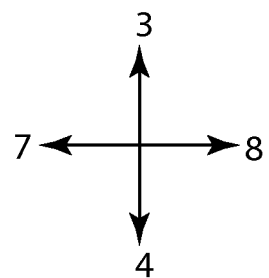

Referring to FIGS. 23 and 24, another alternate embodiment of a prosthetic knee 210 includes the same or similar components of the previous embodiments with a femoral implant 212, a tibial baseplate 214, a tibial insert 216 and a cam post 219 comprising a cam post core 218 and a sleeve 220. This specific embodiment is intended to prevent varus/valgus displacement and may be more suitable for those patients who have insufficient, lax or absent medial or lateral stabilizing ligaments. The tibial insert has a tibial insert channel 215 (similar to those channels 26 and 130 in the two previous embodiments) and a boss 217 (similar to those bosses 24 and 132 of the previous embodiments). The tibial baseplate 214 has a cavity toward the medial side 213

Figure 25:
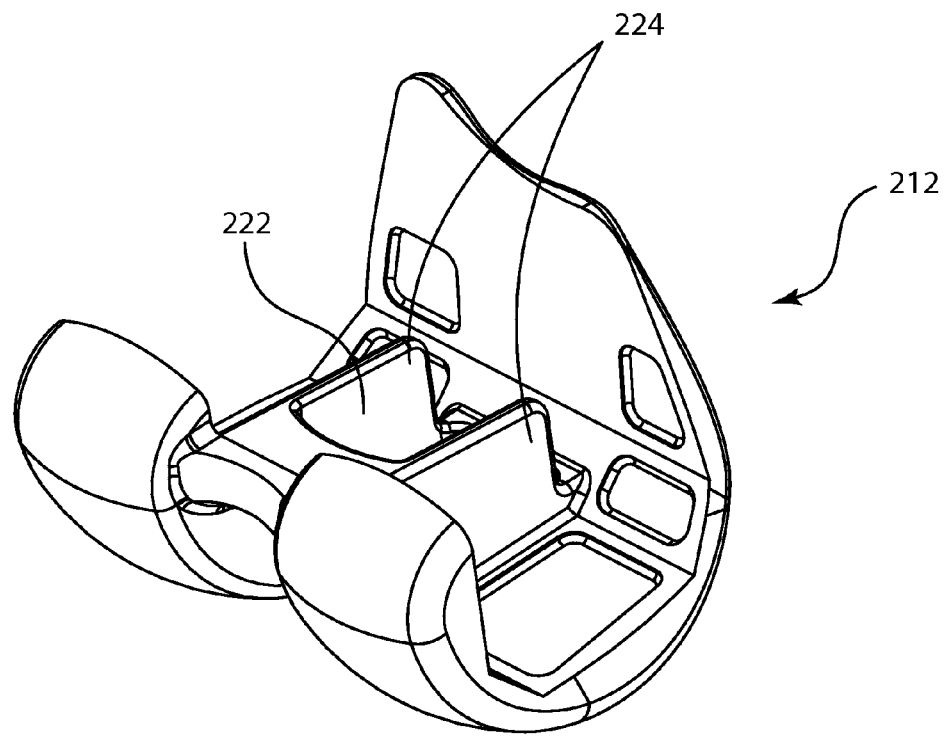
FIG. 25 illustrates a perspective back view of a femoral implant with a femoral opening engaging the cam post and opening walls for stabilization of the cam post and the prosthesis.
Figure 25:
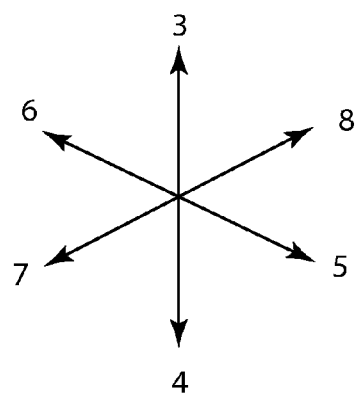

The components are substantially similar to the previous embodiments. The tibial insert has a tibial insert channel 215 (similar to those channels 26 and 130 in the two previous embodiments) and a boss 217 (similar to those bosses 24 and 132 of the previous embodiments). However, referring to FIG. 25, the femoral implant 212 which has a femoral opening 222 may also comprise opening walls 224 which engage the cam post sleeve 220 of the cam post 219 preventing varus/valgus distraction and provide greater medial/lateral stabilization (refer to FIG. 23).

Figure 26:
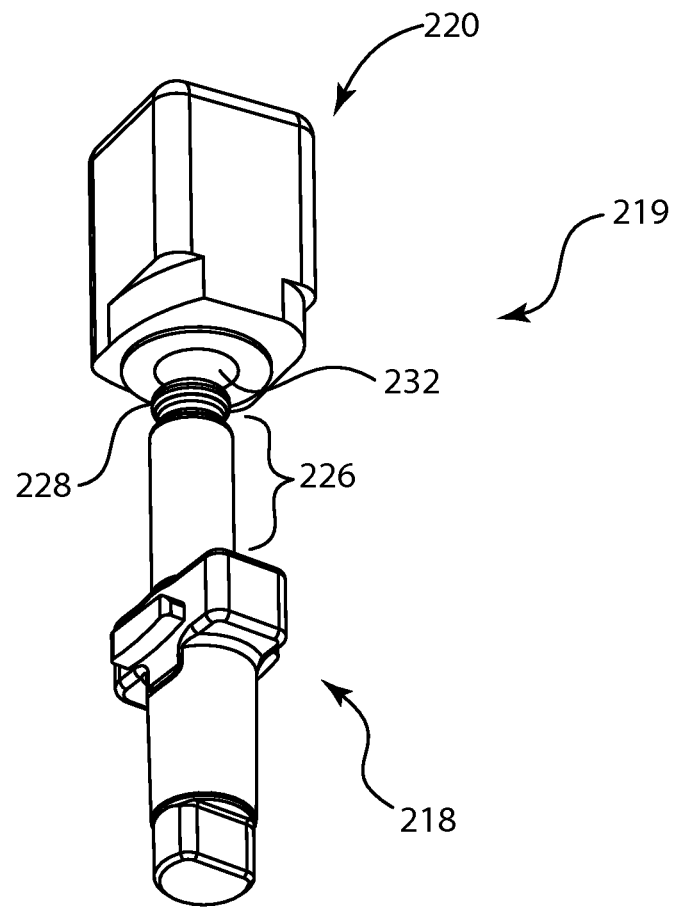
FIG. 26 illustrates a perspective view of the cam post of FIG. 23 with a cam post core with a snap feature for engaging a cam post sleeve.
Figure 26:
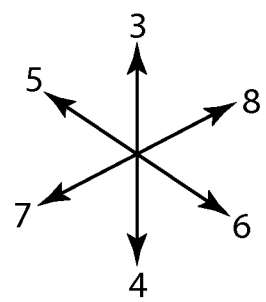

Referring to FIG. 26, the cam post core 218 comprises most of the same features of the cam post core 18 of FIGS. 13 and 14; however, a cam post core superior portion 226 may be substantially circular in cross section with a snap feature 228 on the superior end shaped to snap into engagement with the sleeve 220. The sleeve 220 may be substantially rectangular in cross section, however any shape that would enable engagement with the femoral implant 212 opening walls 224 is sufficient. The sleeve 220 has a cylindrical bore 232 passing longitudinally there through and a taper 230 toward the inferior end of the sleeve 220 to prevent any obstruction of the sleeve with the tibial insert channel 215. The superior portion 226 is at least partially inserted into the sleeve 220 until the two components snap into engagement. The sleeve 220 may rotate around the center axis of cam post core 218 after the sleeve is positioned around the superior portion 226. The cam post core 218 may be polished to minimize wear between the cam post core 218 and the sleeve 220. Internal stops (not shown) may be added to prevent complete rotation of the sleeve around the center axis of the cam post core 218.

Figure 27:
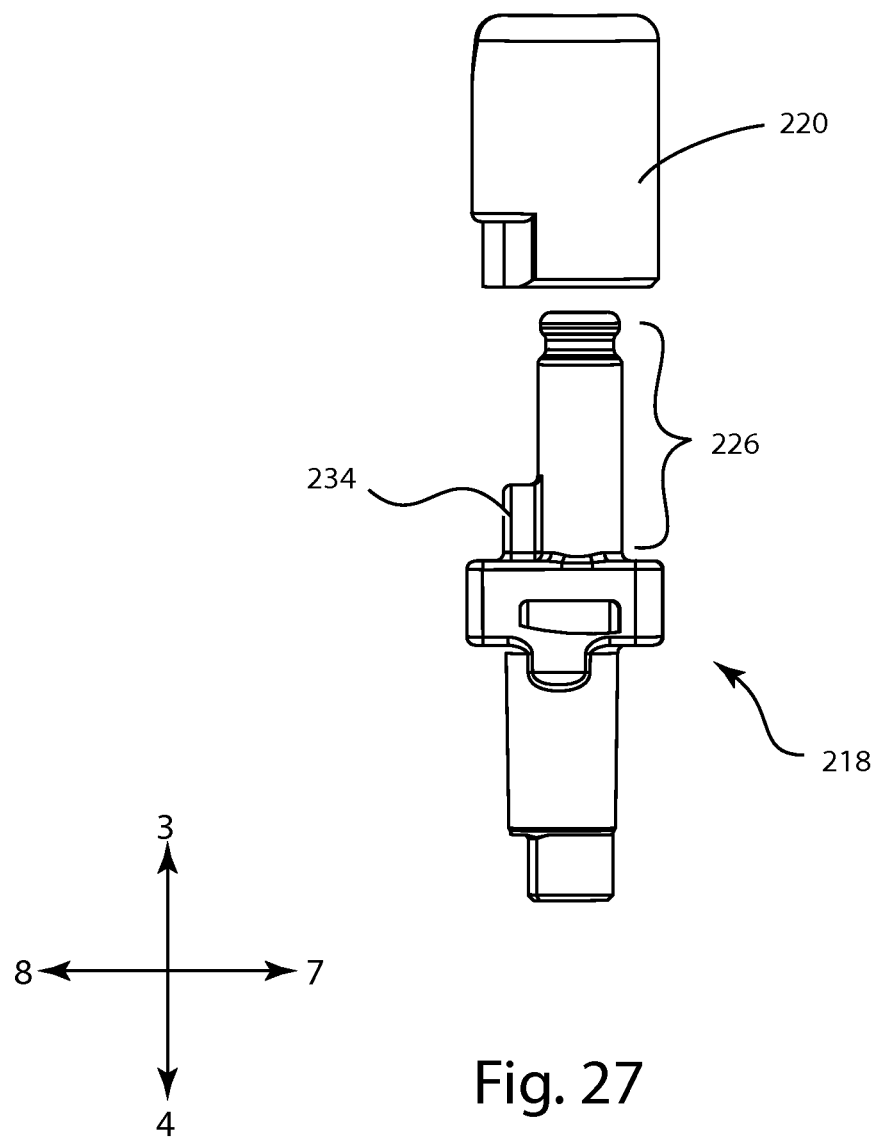
FIG. 27 illustrates a side view of an alternate embodiment of a cam post of FIG. 26 with a cam post sleeve and a cam post core the cam post core having a ridge to prevent movement of the cam post sleeve after it engages the cam post core.
Figure 28:
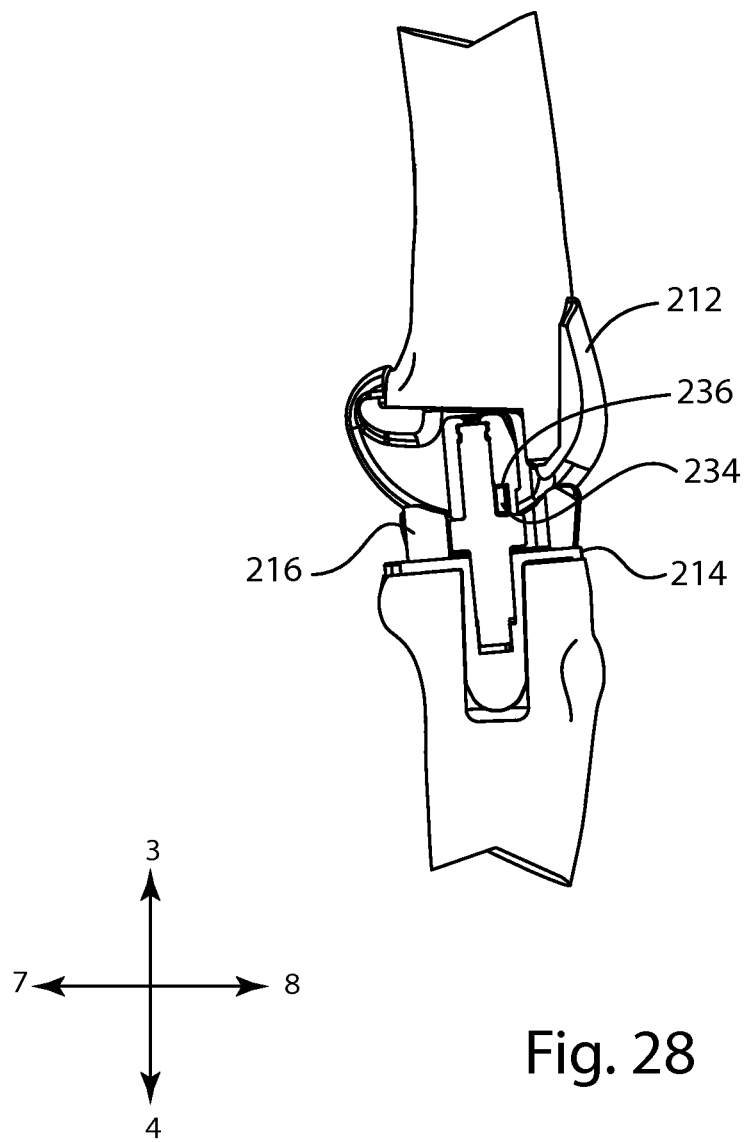
FIG. 28 illustrates slightly different embodiment of the prosthesis of FIG. 23 (the only difference is in the cam post of FIG. 26) showing the cam post of FIG. 27.

Referring to FIGS. 27 and 28, an alternate embodiment of the cam post core 218 may have a ridge 234 which may extend either posteriorly or anteriorly from the superior portion 226 of the cam post core 218. The sleeve 220 may provide a complimentary fit shaped bore 236 that concentrically fits the superior portion 226 with the ridge 234 of the cam post core 218. This ridge 234 prevents any rotational movement of the sleeve 220. Any other means may be used to prevent rotational movement of the sleeve 220 around the cam post core 218. Again, the cam post core 218 and the sleeve 220 may be one piece instead of two pieces.

Figure 29:
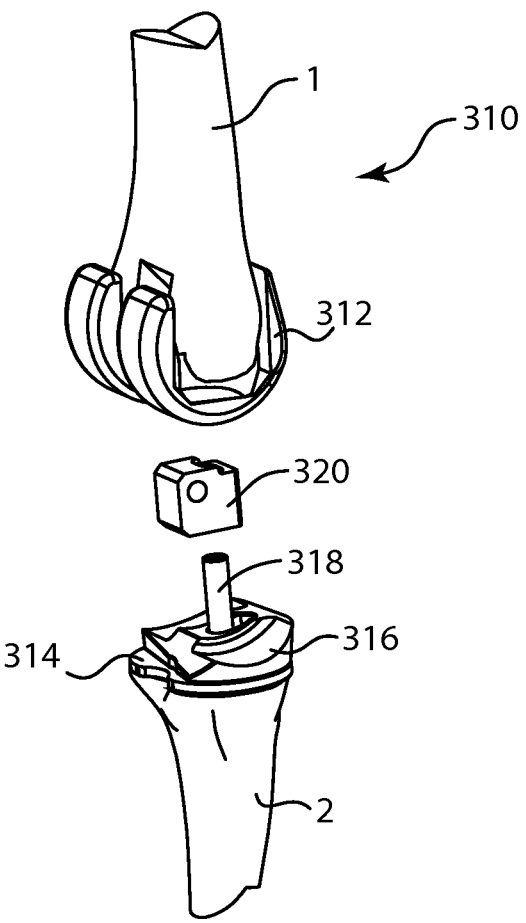
FIG. 29 illustrates an exploded perspective back view of an alternate embodiment of the prosthesis of FIG. 1 with a femur, a tibia, a femoral implant, a tibial insert, a tibial baseplate, a cam post and a hinge block which slides around the cam post.
Figure 29:
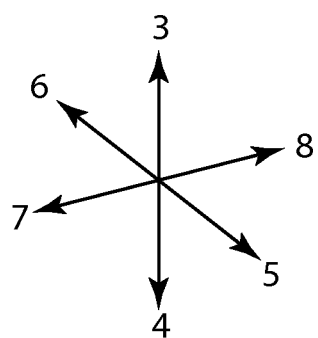
Figure 30:
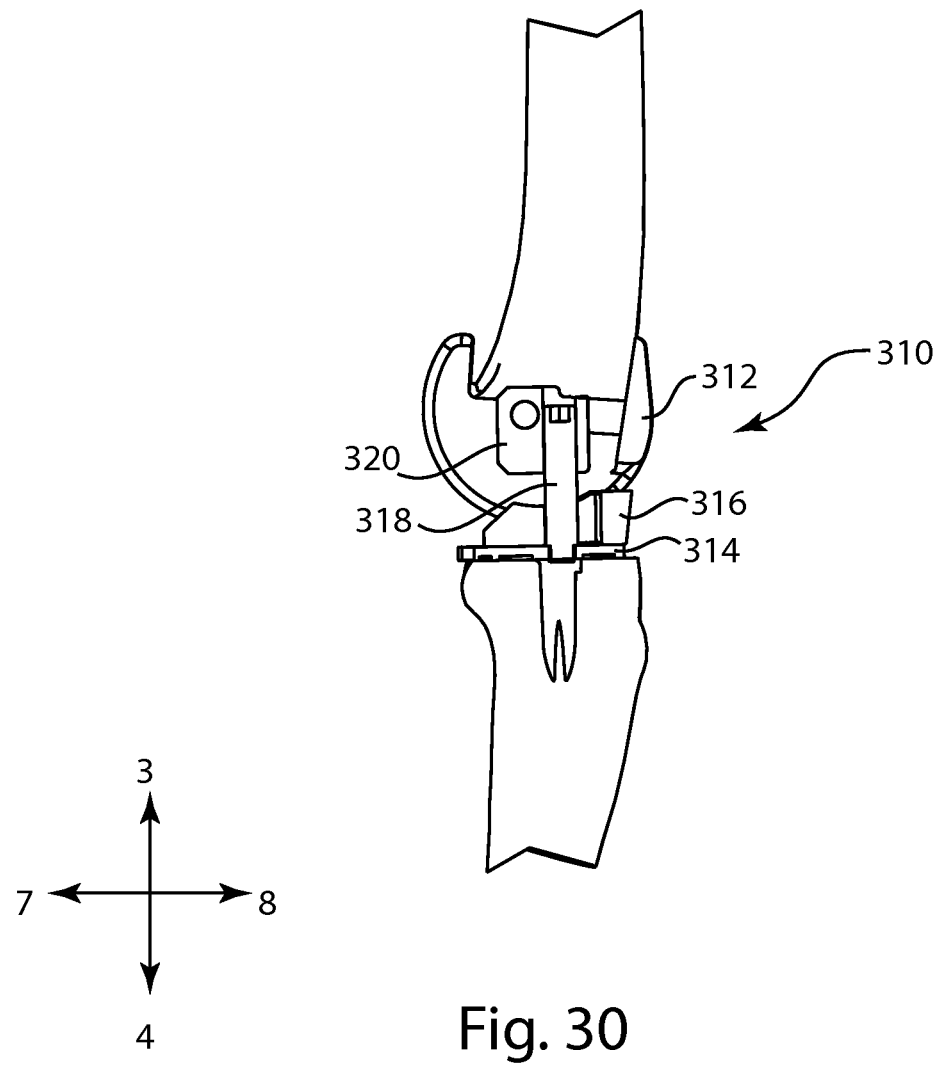
FIG. 30 illustrates a cross section side view of the prosthesis of FIG. 29 with the femoral implant secured to the femur, the femoral implant engaging the hinge block, the hinge block around the cam post, the condyles of the femoral implant articulating against the tibial insert, the tibial insert engaging the tibial baseplate and the tibial baseplate secured to the tibia.
Figure 31:
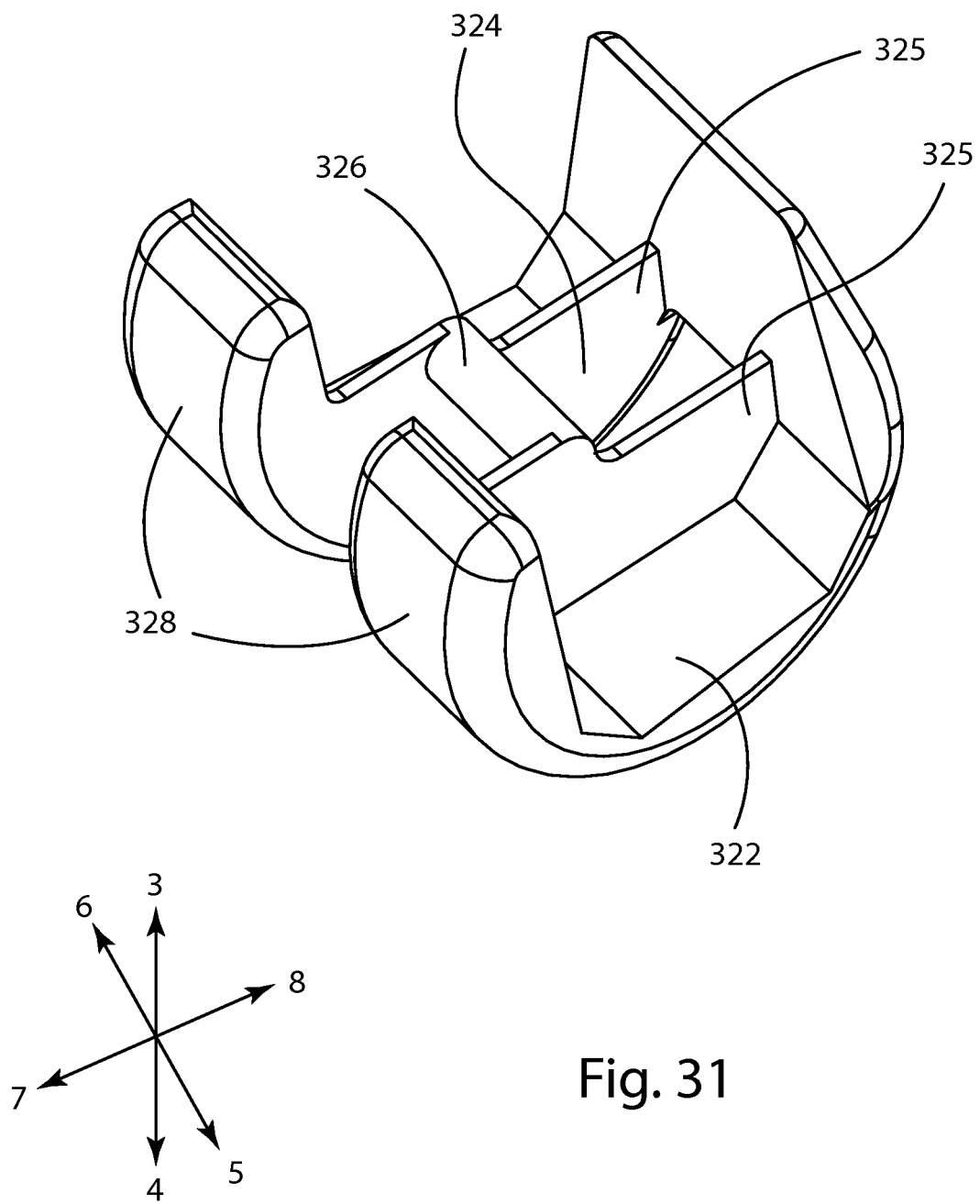
FIG. 31 illustrates a perspective back view of the femoral implant of FIG. 29 with condyles, an opening, opening walls to restrain varus/valgus movement, and an eccentric pin to pass through an opening in the hinge block to stabilize the hinge block (and the prosthesis) within the femoral implant.

Referring to FIGS. 29 and 30, a further embodiment of a prosthetic knee 310 includes a femoral implant 312, a tibial baseplate 314, a tibial insert 316, a cam post 318 and a hinge block 320. The tibial baseplate 314 and the tibial insert may substantially mirror any of the previous embodiments recited herein with the medial rotational axis. Referring to FIG. 31, the femoral implant 312 is similar to the previous embodiments recited herein with a femur facing side 322, a femoral implant opening 324 and condyles 328 match the curvature of the specific tibial insert 316 chosen for the patient's mobility requirements. However, the femoral implant 312 also includes an eccentric pin 326 which is insertable into the hinge block 320 and opening walls 325 which engage the hinge block and help in preventing varus/valgus displacement and axial distraction, and provide greater medial/lateral stabilization (refer to FIG. 29).

Figure 32:
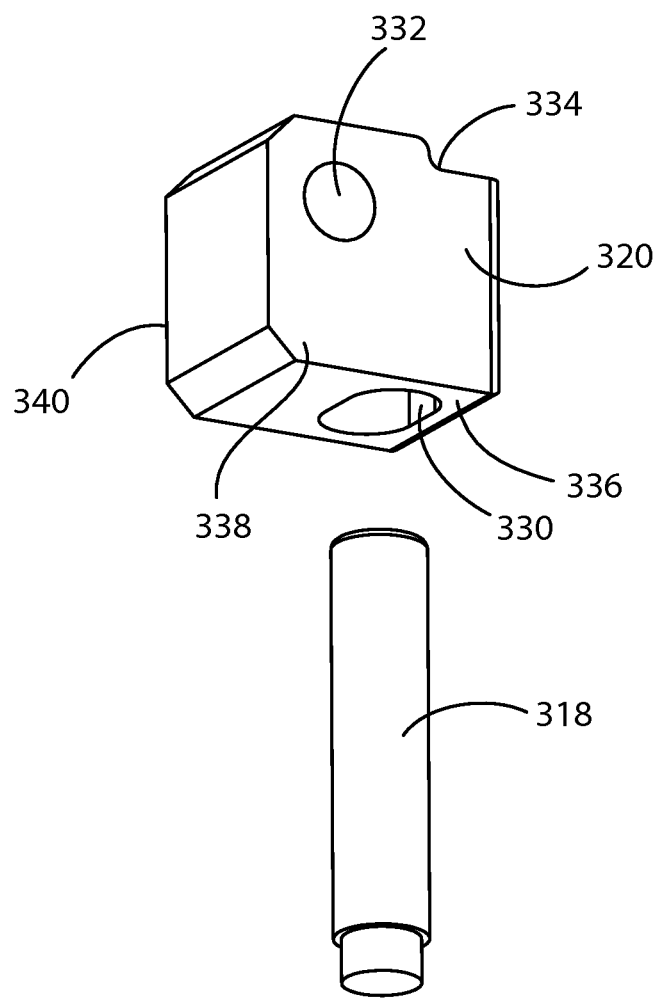
FIG. 32 illustrates a perspective view of the hinge block and cam post of FIG. 29 with the hinge block with a first bore running superiorly/inferiorly for engaging the cam post and a second bore running medial/laterally for engaging the eccentric pin of the femoral implant.

Referring to FIG. 32, the cam post 318 may be substantially circular in cross section with a Morse taper or similar taper toward the inferior end. The hinge block 320 may be substantially rectangular in cross section and may include a first bore 330 extending superiorly/inferiorly through the block from the superior end 334 to the inferior end 336. The first bore 330 is positioned toward the anterior end of the block 320 while the second bore is positioned near the posterior end and superior end 334. The first bore 330 is shaped to slidably receive the cam post 318. The hinge block may also include a second bore 332 extending laterally/medially through the block 320 from the medial end 338 to the lateral end 340. The second bore is positioned and shaped to receive the eccentric pin 326 of the femoral implant 312. The eccentric pin 326 and the opening walls 325 of the femoral implant 312 provide greater medial/lateral stabilization and prevent varus/valgus distraction. The two bores 330, 332 of the hinge block 320 do not intersect. This embodiment may be preferred for those patients that have insufficient, lax or absent medial or lateral stabilizing ligaments.

One method that may be used in placing the prosthetic knee 10 (any of the embodiments will be similar) is to attach the femoral implant 12 and tibial baseplate 14 first to the resected femur 1 and tibia 2 respectively. The order in which either of these is done is left to the preference of the surgeon. After each of the femoral implant 12 and tibial baseplate 14 is secured a trial tibial insert (not shown) with an attached trial cam post (not shown) is positioned on the tibial baseplate to determine the correct size of post and tibial insert to provide for the patients anatomy. The trial cam post is not rigidly connected to the trial insert and can move within the trial tibial insert channel. The trial tibial insert and cam post are removed and the tibial insert 316 is attached to the tibial baseplate through use of the tibial insert boss 24 and the tibial baseplate cavity 22. The knee is the hyper-flexed to allow the cam post 19 to be passed through the tibial insert channel 26 and secured to the tibial baseplate 14 in the tibial baseplate hole 30. The knee is then extended to position the cam post 19 in the femoral implant opening 74.

While this method may be the preferred method, other methods may also be performed such as first attaching the cam post 19 to the tibial baseplate 14 and then passing the tibial insert 16 over the cam post 19. The tibial insert 16 may then be secured to the tibial baseplate 14 and the knee extended to engage the cam post 19 with the femoral implant opening 74.

The present invention may be embodied in other specific forms without departing from its spirit or essential characteristics. It is appreciated that various features of the above described examples and embodiments may be mixed and matched to form a variety of other combinations and alternatives; for example, using the cam post 19 with the tibial insert 116. It is also appreciated that this system should not be limited simply to total knee prosthesis. As such, the described embodiments are to be considered in all respects only as illustrative and not restrictive. The scope of the invention is, therefore, indicated by the appended claims rather than by the foregoing description. All changes which come within the meaning and range of equivalency of the claims are to be embraced within their scope.

The invention claimed is:

1. A knee replacement system comprising:
   a tibial baseplate comprising a tibia facing surface and a superior surface, wherein the tibia facing surface is shaped to lie against a tibial resected surface;
   a femoral knee implant comprising a pair of condyles, a cam feature, and a bone facing side shaped to lie against a resected surface of a femur;
   a tibial insert comprising a baseplate facing side, a lateral articulating surface, and a medial articulating surface, wherein the baseplate facing side pivotally articulates with the superior surface, wherein the baseplate facing side defines a boss toward a medial side to provide a medially-displaced axis of rotation upon insertion of said boss into a cavity positioned medially on the superior surface, wherein the articulating surfaces are shaped and positioned to articulate with the condyles, and a channel passes through the tibial insert along a direction generally perpendicular to the baseplate facing side, wherein the channel is arc shaped to guide a rotation of the tibial insert posteriorly relative to the tibial baseplate about the medially-displaced axis of rotation; and
   a cam post coupled to the tibial baseplate and protruding from the superior surface and passing through the channel, wherein contact of an anterior side of the cam feature with a posterior side of the cam post during flexion of a knee joint in which the knee replacement system is implanted provides the rotation, and
   wherein the cam post further interacts with the channel to provide anterior and posterior stops for the rotation.

2. The knee replacement system of claim 1, wherein the superior surface further defines a hole, wherein the cam post comprises an inferior end shaped to be inserted into the hole during implantation of the knee replacement system.

3. The knee replacement system of claim 2, wherein the cam post comprises a cam post core comprising the inferior end, and an outer sleeve that receives a superior end of the cam post core such that the outer sleeve is fixedly attached to the cam post core, wherein the outer sleeve articulates with the cam feature.

4. The knee replacement system of claim 3, wherein the outer sleeve includes a snap fit feature, wherein the outer sleeve is snapped into engagement with the cam post core.

5. The knee replacement system of claim 3, wherein the outer sleeve has an inferior end, wherein the outer sleeve inferior end has a sleeve notch which receives a portion of the cam post core and stops rotation of the outer sleeve when the outer sleeve is snapped into engagement with the cam post core.

6. The knee replacement system of claim 2, wherein the cam post comprises a cam post core having a superior portion, an inferior portion and an intermediate portion between the superior and inferior portions, wherein the intermediate portion is enlarged relative to the inferior and superior portions.

7. The knee replacement system of claim 6, wherein the intermediate portion has a bottom surface which rests upon the superior surface.

8. The knee replacement system of claim 6, wherein the intermediate portion comprises a first wing extending medially from the intermediate portion and a second wing extending laterally from the intermediate portion.

9. The knee replacement system of claim 8, wherein the first and second wings are positioned as a stop to engage the outer sleeve.

10. The knee replacement system of claim 1, wherein each of the condyles comprises a radius of curvature defining flexion and extension of the knee joint, wherein each of the medial and lateral articulating surfaces comprises a radius of curvature closely matched to that of the corresponding condyle such that a center of rotation of each condyle remains substantially stationary relative to the corresponding articulating surface during flexion and extension of the knee joint.

11. The knee replacement system of claim 1, wherein the boss is insertable into the cavity along the same direction as the cam post through the channel.

12. The knee replacement system of claim 11, wherein the boss is substantially circular in shape.

* * * * *